United States Patent [19]

Murakami et al.

[11] Patent Number: 5,453,419
[45] Date of Patent: Sep. 26, 1995

[54] *XENOPUS LAEVIS* BONE MORPHOGENETIC PROTEINS AND USE THEREOF

[75] Inventors: Kazuo Murakami; Naoto Ueno, both of Ibaraki; Yukio Kato, Osaka, all of Japan

[73] Assignee: Chichibu Cement Co., Ltd., Tokyo, Japan

[21] Appl. No.: 56,564

[22] Filed: Apr. 30, 1993

Related U.S. Application Data

[63] Continuation of Ser. No. 577,892, Sep. 5, 1990, abandoned.

[30] Foreign Application Priority Data

Sep. 6, 1989 [JP] Japan .................................. 1-229250
Jul. 20, 1990 [JP] Japan .................................. 2-190774

[51] Int. Cl.⁶ .......................... A61K 38/17; C07K 14/435
[52] U.S. Cl. .......................... 514/12; 530/350; 530/412; 435/69.1
[58] Field of Search .................... 530/350, 412; 514/12; 435/69.1

[56] References Cited

U.S. PATENT DOCUMENTS

| | | | |
|---|---|---|---|
| 4,455,256 | 6/1984 | Urist | 530/355 |
| 4,472,840 | 9/1984 | Jeffories | 623/10 |
| 4,526,909 | 7/1985 | Urist | 514/21 |
| 4,563,350 | 1/1986 | Nathan et al. | 514/21 |
| 4,563,489 | 1/1986 | Urist | 514/21 |
| 4,596,574 | 6/1986 | Urist | 514/21 |
| 4,619,989 | 10/1986 | Urist | 530/355 |
| 4,761,471 | 8/1988 | Urist | 514/21 |
| 4,789,732 | 12/1988 | Urist | 514/21 |
| 4,857,456 | 8/1989 | Urist | 436/86 |
| 4,877,864 | 10/1989 | Wang et al. | 530/324 |
| 5,141,905 | 8/1992 | Rosen et al. | 435/69.1 |

FOREIGN PATENT DOCUMENTS

WO88/00205  1/1988  WIPO.
WO89/09788  10/1989  WIPO.

OTHER PUBLICATIONS

Lyons et al,. PNAS, 86:4554–4558, 1989.
Weeks, D. L., et al., Cell:51, 861–867 (Dec. 4, 1987).
Wozney, J. M., et al., Science 242:1528–1534 (Dec. 16, 1988).

*Primary Examiner*—Garnette D. Draper
*Assistant Examiner*—Sally P. Teng
*Attorney, Agent, or Firm*—David G. Conlin; Ronald I. Eisenstein

[57] ABSTRACT

Disclosed are (1) a *Xenopus laevis* bone morphogenetic protein (BMP), (2) a DNA comprising a DNA segment coding for a *Xenopus laevis* BMP, (3) a transformant bearing a DNA comprising a DNA segment coding for a *Xenopus laevis* BMP and (4) a method for preparing the *Xenopus laevis* BMP which comprises culturing the described in (3), producing and accumulating the protein in a culture, and collecting the protein thus obtained. Cells transfected or transformed with the DNA allow large amounts of the *Xenopus laevis* BMP mature peptides to be produced, which causes the advantageous production of the peptides, which promote the synthesis of proteoglycan and can also be utilized for analysis of the mechanism of organism, particularly human bone-cartilage morphogenetic reaction, and as therapeutic agents for osteoporosis.

18 Claims, 18 Drawing Sheets

```
         10        20        30        40        50        60
TTTCCAGTCTGATTTGCAGTGATACTTTACAATACAATAGGGAAGAAACAAGAAAATATA
         70        80        90       100       110       120

AGTATANNTAAAGTGATTAAGCATAAGAGAATCGGTATTAACNTGATCNTGTCAANTGTG 130       140       150       160       170       180
TCAATCTAATGTAAAGCAAAACTCTTAAGNTCATTGGCTAATACTGTTNTGTNTGCCTTT
                                        CysLeuPhe 190       200       210       220       230       240
TCTGTCAATATTCAGGACCATCCAAGAAAGTACTGCGCTTTGAAATTTCCAAAGAAGGCA
  CysGlnTyrSerGlyProSerLysLysValLeuArgPheGluIleSerLysGluGlySer 250       260       270       280       290       300
GTAACTTTTTAATTATTGGTGAAGCGGACCTTTGGCTGTTCCTAAAGTTGTCCAAGGCTA
  AsnPheLeuIleIleGlyGluAlaAspLeuTrpLeuPheLeuLysLeuSerLysAlaAsn 310       320       330       340       350       360
ATCGAAGTCGCACCAAACTGACTATACGATTGTACCACCAGCAAAGAGGTCAGAAAGACC
  ArgSerArgThrLysLeuThrIleArgLeuTyrHisGlnGlnArgGlyGlnLysAspGln 370       380       390       400       410       420
AGCGTGGATCTGAGAGCAACAAAAGTGAACTGCTTATTGCAGAAAAAGTAGTGGATACAA
  ArgGlySerGluSerAsnLysSerGluLeuLeuIleAlaGluLysValValAspThrArg 430       440       450       460       470       480
GGAAAAGTGGATGGCATACGTTTCCCATAGCTGGTAGCATCCAACGTTTACTTAATTATG
  LysSerGlyTrpHisThrPheProIleAlaGlySerIleGlnArgLeuLeuAsnTyrGly 490       500       510       520       530       540
GCAAATCAACCATAGATATCAGAGTAGCTTGTGATCAATGCCAGGAGGCAGGGGCTACAC
  LysSerThrIleAspIleArgValAlaCysAspGlnCysGlnGluAlaGlyAlaThrPro 550       560       570       580       590       600
CTGTCTTGCTTGGAAAAAGGAAGAAGAAGGACGATGAAGACAAAGAAGCAGGGGTATCAG
  ValLeuLeuGlyLysArgLysLysLysAspAspGluAspLysGluAlaGlyValSerGly 610       620       630       640       650       660
GTGCAGAAGAAGAAAAAGAGCAATCACATAGGCCTTTCCTAATGATTGTGGCCCGGCAGA
  AlaGluGluGluLysGluGlnSerHisArgProPheLeuMetIleValAlaArgGlnThr 670       680       690       700       710       720
CAGATGAGCACCCCCATAGAAGAAAAAAACGTGGCTTAGAGTGTGATGGTAAAGTTAGCA
  AspGluHisProHisArgArgLysLysArgGlyLeuGluCysAspGlyLysValSerIle 730       740       750       760       770       780
TTTGTTGCAAGAAGCATTTCTACGTCAGCTTCAAAGACATTGGTTGGAGTGATTGGATCA
  CysCysLysLysHisPheTyrValSerPheLysAspIleGlyTrpSerAspTrpIleIle
```

Fig.2(1)-2

```
         790       800       810       820       830       840
TAGCACCTCCTGGCTACCATGCCAATTATTGTGAGGGAGACTGCCCTAGCCATATTGCTG
  AlaProProGlyTyrHisAlaAsnTyrCysGluGlyAspCysProSerHisIleAlaGly 850       860       870       880       890       900
GAACTACTGGCTCATCCTTGTCTTTTCACTCCACAGTTATAAACCAGTACAGACTAAGGG
  ThrThrGlySerSerLeuSerPheHisSerThrValIleAsnGlnTyrArgLeuArgGly 910       920       930       940       950       960
GCCAAAGTCCCTTCACCAGCATCAAATCCTGCTGTGTGCCCTCTAAGCTTAGAGCTATGT
  GlnSerProPheThrSerIleLysSerCysCysValProSerLysLeuArgAlaMetSer 970       980       990      1000      1010      1020
CCATGTTGTACTATGATGACGGTCAGAATATAATCAAAAAGGATATTCAAAATATGATTG
  MetLeuTyrTyrAspAspGlyGlnAsnIleIleLysLysAspIleGlnAsnMetIleVal 1030      1040      1050      1060      1070      1080
TGGAGGAATGTGGCTGCTCATAAAGTTAAAAAGAGCATTGTCATTGTCAGCATTGCGTTG
  GluGluCysGlyCysSer***

1090      1100      1110      1120      1130      1140
AAAATACACTAATCAAGAGAAGTGCAAATGAACAAAGATCAAAAGTCAAAGTTATCAGGG 1150      1160      1170      1180      1190      1200
TTTGGGTGGTGAACTTGATTCACAGTAAACAGCCTGCAGCAATTTTTATCCAAACGTGGA 1210      1220      1230      1240      1250      1260
AACCCCTTTTTAAGCACGACTGTGGATTTTATTTTAAATAAAAGCACAAGAACANATATA 1270      1280      1290      1300      1310      1320
AAGCTATTTATAAAATGTTTGCATATCTGACAGGTGCTTCTGTTACTGCACATGCGGGTA 1330      1340      1350      1360      1370      1380
TACANATGTGTATAAATAGGTACACTGTAAAGATATCCAGAGAGTCATGTTTGATGCCAT 1390      1400      1410      1420      1430      1440
GTTGTCAGTCAGCAGTTCATAGTTTCAGAAGATAAATACATTGCGCAGGTAATCTCACCT 1450      1460      1470      1480      1490      1500
TCTTCCTCTGCACTATCCTTGCAAAAGTATAAAAAATACAGAAAAAGGCAAACAAAGTT 1510      1520      1530      1540      1550      1560
AAATTTCACTACGGTGCTGATGATCATAGAACTATGCAACTTTTTGGGTTTGAAAACCGT 1570      1580      1590      1600      1610      1620
TTACCTGAGAATTAAAAGAGAGACTTTTACAGTGGAAGCAACGTAAATATTTTTGTTCTT 1630      1640      1650      1660
TCATGAGAGATACTTGAAAGGAACATGTTGGTCCAGGTTCTGGATCC
```

```
         10        20        30        40        50        60
AAGCTTACAGTTGGAATTGAACTGTGATGGATGCCAAGATGTGCCAGTTTTAGCCAATCC
  SerLeuGlnLeuGluLeuAsnCysAspGlyCysGlnAspValProValLeuAlaAsnPro 70        80        90       100       110       120
CAATAATTCCCACCAGCCATTTCTGGTAGCACAGGCCAAAGTCCATGAACAAAGTCACCA
  AsnAsnSerHisGlnProPheLeuValAlaGlnAlaLysValHisGluGlnSerHisHis 130       140       150       160       170       180
TGCTACAAAGAGAAGTCTTAACTGTGATCAGAACTCCAATCTGTGCTGTAGGAAAGACTA
  AlaThrLysArgSerLeuAsnCysAspGlnAsnSerAsnLeuCysCysArgLysAspTyr 190       200       210       220       230       240
TTATGTAGACTTCAAGGATATTGGGTGGAATGATTGGATTATAAAACCAGAGGGATATCA
  TyrValAspPheLysAspIleGlyTrpAsnAspTrpIleIleLysProGluGlyTyrGln 250       260       270       280       290       300
GATAAATTATTGCATGGGCCTTTGCCCAATGCATATCCCTGGAGCCCCAGGTACGGGAGG
  IleAsnTyrCysMetGlyLeuCysProMetHisIleAlaGlyAlaProGlyThrAlaAla 310       320       330       340       350       360
CTCATTCCACACCACGGTATTAAATCTCATTAAGGCCAACAATATCCAGACAGCAGTGAA
  SerPheHisThrThrValLeuAsnLeuIleLysAlaAsnAsnIleGlnThrAlaValAsn 370       380       390       400       410       420
CTCATGCTGTGTCCCTACCAAAAGGCGCCCTTTGTCCATGCTTTACTTTGATAGAAATAA
  SerCysCysValProThrLysArgArgProLeuSerMetLeuTyrPheAspArgAsnAsn 430       440       450       460       470       480
CAACGTTCTCAAGACTGACATTGCCGATATGATTGTGGAAGCCTGTGGGTGTAGCTAGGG
  AsnValLeuLysThrAspIleAlaAspMetIleValGluAlaCysGlyCysSer***

490       500       510       520       530       540
CTTGGGCTACATCAGTTTGGGACATTTACAATAAAAAAGAGGGAAGCTGGCTTTTCTCTT 550       560       570       580       590       600
CATTATTTGCTCGAGATGCTTTAGACAGGTGAAGAACAAGTGAAAAAACTGATTCCACAT 610       620       630       640       650       660
TCACTTATCAAATTCATGGGAATCGTTAACANGATCANCCTCTCTAAACGGATCTAGGGA 670       680
GCTGTAGCACAATANCTNTCCAGCAGG
```

Fig.2(3)-1

```
              C4
       10        20        30        40        50        60
AGAGCAGGTCAAGAGCCCTTTGANAGTGACAGCAGCAAATTGCATCGGATTANTATTTAC 70        80        90       100       110       120
GACATTGTCAGGSCAGCGGNNNNCTGGSCTSCCGGGGGCCTGTTGTGAGACTATTGGACA
                                      ArgGlyProValValArgLeuLeuAspThr 130       140       150       160       170       180
CCAAACTGGTACATCATAATGAAAGCAAATGGGAAAGTTTTGATGTAGCGCCGGCAATTG
 LysLeuValHisHisAsnGluSerLysTrpGluSerPheAspValAlaProAlaIleAla 190       200       210       220       230       240
CGCGGTGGATTGCACATAAACAGCCTAACCATGGGTTTGTTGTTGAAGTTACTCACTTGG
 ArgTrpIleAlaHisLysGlnProAsnHisGlyPheValValGluValThrHisLeuAsp 250       260       270       280       290       300
ACAATGACAAAAATGTGCCTAAGAAGCATGTGAGGATTAGTAGGTCTTTAACCCCGGATA
 AsnAspLysAsnValProLysLysHisValArgIleSerArgSerLeuThrProAspLys 310       320       330       340       350       360
AAGATAACTGGCCTCAGATACGGCCATTGTTGGTAACTTTTAGCCATGATGGTAAAGGAC
 AspAsnTrpProGlnIleArgProLeuLeuValThrPheSerHisAspGlyLysGlyHis 370       380       390       400       410       420
ATGCTCTTCACAAAAGACAAAAGCGCCAAGCTAGGCACAAACAACGTAAACGCCTTAAAT
 AlaLeuHisLysArgGlnLysArgGlnAlaArgHisLysGlnArgLysArgLeuLysSer 430       440       450       460       470       480
CGAGCTGCAGGAGGCATCCGTTGTACGTAGATTTCAGCGACGTTGGTTGGAATGACTGGA
 SerCysArgArgHisProLeuTyrValAspPheSerAspValGlyTrpAsnAspTrpIle 490       500       510       520       530       540
TTGTTGCCCCACCTGGGTATCATGCCTTTTACTGCCACGGGGAATGTCCTTTTCCACTGG
 ValAlaProProGlyTyrHisAlaPheTyrCysHisGlyGluCysProPheProLeuAla
```

Fig.2(3)-2

```
         550        560        570        580        590        600
CAGACCATTTAAACTCTACAAACCATGCAATCGTACAAACTTTGGTGAACTCTGTCAACA
  AspHisLeuAsnSerThrAsnHisAlaIleValGlnThrLeuValAsnSerValAsnThr 610        620        630        640        650        660
CAAACATCCCCAAAGCTTGCTGCGTCCCCACAGAACTCAGTGCCATATCCATGCTCTATC
  AsnIleProLysAlaCysCysValProThrGluLeuSerAlaIleSerMetLeuTyrLeu 670        680        690        700        710        720
TTGATGAGAATGAAAAAGTAGTATTAAAAAATTATCAAGACATGGTCGTGGAGGGGTGCG
  AspGluAsnGluLysValValLeuLysAsnTyrGlnAspMetValValGluGlyCysGly 730        740        750        760        770        780
GATGCCGTTAGGCAGTTACGCGCAAGCCAGAGACAAGAAAGATGACACTTTAATATTTCC
  CysArg***

790        800        810        820        830        840
TTTTGGAGACTATATTTATGCTTTGAAAAATGATGAAACANTTATTTTGAAAATATATTT 850        860        870        880        890        900
ATGTCTACACGGAGGTTGGGAAGCAAATATTTAATCAGAGAAATATTCCTTTTTTTAGT 910        920        930        940        950
TGTACATTTTTATAAGGGTTTGTACCCAGCACATGAAGTATAATGGTCAGATTGA
```

Fig.2(4)

A4
```
         10        20        30        40        50        60
CCTGAGANTTAAGAAGTGTGGGATTTAACAGAACAGGACGACCGACCAATGAGAAAGCTA 70        80        90       100       110       120
TTTTTCTTGTCTNTGGTAGGACAAAGAAACGGGACNTGTTCTTCAATGAGATTAAAGCCA
                      PhePheAsnGluIleLysAlaArg 130       140       150       160       170       180
GGTCTGGCCAAGATGACAAGACTGTCTATGAATATTTATTCAATCAGAGGAGAAAGAGAC
  SerGlyGlnAspAspLysThrValTyrGluTyrLeuPheAsnGlnArgArgLysArgArg 190       200       210       220       230       240
GAGCTCCTCTGTCAACTAGGCAAGGGAAGAGGCCTAATAAGAATTCAAAAGCAAGATGTA
  AlaProLeuSerThrArgGlnGlyLysArgProAsnLysAsnSerLysAlaArgCysSer 250       260       270       280       290       300
GCAAGAAACCACTTCATGTCAATTTCAAGGATATGGGTTGGGATGATTGGATTATTGCCC
  LysLysProLeuHisValAsnPheLysAspMetGlyTrpAspAspTrpIleIleAlaPro 310       320       330       340       350
CTTTGGAGTATGAGGCATATCATTGTGAAGGGCTTTGTGAGTTCCCTCTGAGATCT
  LeuGluTyrGluAlaTyrHisCysGluGlyLeuCysGluPheProLeuArgSer
```

```
         10        20        30        40        50        60
AAGCTTTACTGGTGGTGTCTTCCCATTCCAAGAGGAGGGAAAACTTGTTTAAGGAGATCA 70        80        90       100       110       120
GGGACAAGATTAAGTCAATTGGAAATCCTAAATTCTTGGAGCCACCGGATTCAGTCAACA
               IleLeuGlyAlaThrGlyPheSerGlnGln 130       140       150       160       170       180
GTCCATCGCCAAGAGGAGATGGAAACGAACAACTCTCCCCACTAGGACAAATAATGGCAA
 SerIleAlaLysArgArgTrpLysArgThrThrLeuProThrArgThrAsnAsnGlyLys 190       200       210       220       230       240
AGGTCATGCGAAGAAATCCAAAACAAGGTGTAGCAAGAAGCCCCTTCTTGTCAACTTCAA
 GlyHisAlaLysLysSerLysThrArgCysSerLysLysProLeuLeuValAsnPheLys 250       260       270       280       290       300
GGAGTTGGGTTGGGATGACTGGATTATTGCTCCCTTGGATTATGAAGCCTATCACTGCGA
 GluLeuGlyTrpAspAspTrpIleIleAlaProLeuAspTyrGluAlaTyrHisCysGlu 310       320
GGGGGTCTGTGATTTCCCACTGAGATCT
 GlyValCysAspPheProLeuArgSer
```

Fig.2(6)-1
pxbr22(BMP2A)

```
         10         20         30         40         50         60         70         80         90        100
GAATTCTCTTCCCTCTCACCGGCCTCTGTCTCTACTCACCTCCCGGGGACCCCGGCTGGACTGAGACACTGCTGCCACTATGTGCGACAACTCACCGA 110        120        130        140        150        160        170        180        190        200
CTGGGCTCGACTGGACGGCGGGGACTTGTCTCCCCTCCTCTGGGACCAGCACTTGAACTAAAGACTCGAGTGATTGTGAAAAACACGCGGGGAGCAGA 210        220        230        240        250        260        270        280        290        300
AAACCCACATGCGAGACACAAACTCGGGACTAAATCGCTCAGGTTGACAATGTCGCTGGGATCCACTCTCTGCTGCTCTGCCAGTTTTACCAGATCTTG
                                            M  V  A  G  I  H  S  L  L  L  Q  F  Y  Q  I  L 310        320        330        340        350        360        370        380        390        400
CTGAGCGGCTGCACCGGGCTCGTCCCAGAGGAAGGCAAACGCAAGTATTCCGAATCCACTCGCTGTCTCCGCAGCAGTCCCAACAAGTCCTCGACCAGT
 L  S  G  C  T  G  L  V  P  E  E  G  K  R  K  Y  S  E  S  T  R  S  S  P  Q  Q  S  Q  V  L  D  Q  F 410        420        430        440        450        460        470        480        490        500
TTGAGCTTCGGCTGCTCAATATGTTCGGCTTGAAGAGACGACCTACAGGGCAAAAATGTTGTGATCCCCCTACATGTTGGACTTGTACCACCTGCA
 E  L  R  L  L  N  M  F  G  L  K  R  R  P  T  P  G  K  N  V  V  I  P  P  Y  M  L  D  L  Y  H  L  H 510        520        530        540        550        560        570        580        590        600
CTCGGCTCAGTTGGCCGATGATCAAGGAAGTTCTGAGGTGGACTATATCACATGAGCGGGGCTAGCAGAGCCAACACAGTGAGGAGCTTTCACCATGAA
 S  A  Q  L  A  D  D  Q  G  S  S  E  V  D  Y  H  M  E  R  A  A  S  R  A  N  T  V  R  S  F  H  H  E 610        620        630        640        650        660        670        680        690        700
GAATCCATGGAAGAAATTCCAGAGTCTGGTGAGAAAACAATCCAACGATTCTTCTTCAACCTTTCTTCAATTCCAGATGAGGAGCTGGTCACGTCTCTG
 E  S  M  E  E  I  P  E  S  G  E  K  T  I  Q  R  F  F  F  N  L  S  S  I  P  D  E  E  L  V  T  S  S  E 710        720        730        740        750        760        770        780        790        800
AGCTCCGGATTTTTCGAGAGCAGGTCCAAGAGCCATTAAGACTGACGGCAGCAACTTCATGGATTAATATTTATGACATTGTCAAGCCAGCGGCGGC
 L  R  I  F  R  E  Q  V  Q  E  P  F  K  T  D  G  S  K  L  H  R  I  N  I  Y  D  I  V  K  P  A  A  A 810        820        830        840        850        860        870        880        890        900
TGCCTCCCGGGGCCCTGTTGTAAGACTATTGGACACCAGACTGATCATCATATGAAAGCAAATTTGATGACGCGGCAATTACACGG
 A  S  R  G  P  V  V  R  L  L  D  T  R  L  I  H  H  N  E  S  K  W  E  S  F  D  V  T  P  A  I  T  R 910        920        930        940        950        960        970        980        990       1000
TGGATTGCACATAAACAGCCTAACCATGGGTTTGTTGAAGTGACTCACTTGGACAATGACACAAATGTGCCCAAGAGGCATGTGAGGATTAGTAGGT
 W  I  A  H  K  Q  P  N  H  G  F  V  V  E  V  T  H  L  D  N  D  T  N  V  P  K  R  H  V  R  I  S  R  S
```

Fig. 2(6)-2
pxbr22(BMP2A)

```
         1010      1020      1030      1040      1050      1060      1070      1080      1090      1100
CTTTAACCCTGGATAAAGGTCACTGGCCTCGGATACGGCCATTATTGGTAACTTTAGCCATGATGGCAAAGGACATGCTCTTCACAAAGACAAAAACG
 L  T  L  D  K  G  H  W  P  R  I  R  P  L  L  V  T  F  S  H  D  G  K  G  H  A  L  H  K  R  Q  K  R 1110      1120      1130      1140      1150      1160      1170      1180      1190      1200
GCAAGCTAGGCACAAACAACGTAAAACGCCTTAAATCGAGCTGCAGGAGGCATCGTTGTACGTAGATTTCAGTGACGTTGGTTGGAATGACTGGATTGTT
 Q  A  R  H  K  Q  R  K  R  L  K  S  S  C  R  R  H  P  L  Y  V  D  F  S  D  V  G  W  N  D  W  I  V 1210      1220      1230      1240      1250      1260      1270      1280      1290      1300
GCCCCACTGGGTATCATGCCTTTTACTGCCACGGGGAATGTCCTTTCCACTGGCAGACCATTAAACTCTACAAACCATGCAATGTACAAACTTTGG
 A  P  P  G  Y  H  A  F  Y  C  H  G  E  C  P  F  P  L  A  D  H  L  N  S  T  N  H  A  I  V  Q  T  L  V 1310      1320      1330      1340      1350      1360      1370      1380      1390      1400
TGAATTCCGTCAACACAAACATTCCCAAAGCTTGCTGCGTCCCCACAGAACTCAGTGCCATCTCCATGCTCTATCTTGATGAGAATGAAAAAGTAGTATT
 N  S  V  N  T  N  I  P  K  A  C  C  V  P  T  E  L  S  A  I  S  M  L  Y  L  D  E  N  E  K  V  V  L 1410      1420      1430      1440      1450      1460      1470      1480      1490      1500
AAAGAATTATCAAGACATGGTCGTTGGAGGGGTGCCGGGGTGCCGTTAGGGGGGACACACAAGCAGAGACAAGAAAGCTGACACTTTATATTTCCTTTTG
 K  N  Y  Q  D  M  V  V  E  G  C  G  C  R  *

1510      1520      1530      1540      1550      1560      1570      1580      1590      1600
GAGACTATATTTATGCTTGAAAATGATGAAACAATTATTTGAAAATATATTTAGTCTACACGGAGGCTGGGAAGCAAATATTTTAATCAGAGAAAT 1610      1620      1630      1640      1650      1660      1670      1680      1690      1700
ATTCCTTTTAGTGTACATTTTTATAAGGGTTTGTACCCAGCACAAGTAATGGTCAGATTCCTATTTGTATTTATTTACCATTATAACCACTT 1710      1720      1730      1740      1750      1760      1770      1780      1790      1800
TTTAAGGAAAAAAATAGCTGTTTGTATTTATATGTAATCAACAGAGAAAATATAGGGTTTGTAAATATGTTACTGAAAGTGTTTTTCTTTTTT 1810      1820      1830      1840      1850      1860      1870      1880      1890      1900
TAAATTATGTATACACAGCTGGTTATATGGCAAGTTTTTTATATTTCTATAAAGCTAATTTCAAGGTCATTAGTTATAAACTTGATGTGTTGGTTC 1910      1920      1930      1940      1950      1960      1970      1980      1990
ATTGGTAAATCCTCCATATTGTGCAATTAACATGCATTTTTATAAGTACGAAGTCCAGTCCATTGTGCTTTGCATTGCTTTGCAAATTTAGAATTC
```

Fig.2(7)-1
pxbr23 (BMP2B)

```
         10         20         30         40         50         60         70         80         90        100
GGAATTCCGGCCCACTGAGCTTTCCACACATTTTTGTGTCAACATTGGCTGTCAAGAATCATGGAATGTTTTCTATGCCTGTTTTCTGTCAAGA
        110        120        130        140        150        160        170        180        190        200
CATCATGATTCCTGGTAACCGAATGCTGATGGTCATTTTATTAAGCCAAGTCCTGCTCGGAGGCACTAACTATGCCAGCCTGATACCTGACACGGGCAAG
  M  I  P  G  N  R  M  L  M  V  I  L  S  Q  V  L  L  G  G  T  N  Y  A  S  L  I  P  D  T  G  K
        210        220        230        240        250        260        270        280        290        300
AAGAAAGTCGCGGCCGACATTCAGGGAGGAGGTCGCGGCCAGTCGCCTCAGAGCAATGAGCTCTTGCGGGATTCGAGGTGACGCTGCAGATGTTCGGAC
  K  K  V  A  A  D  I  Q  G  G  G  R  R  S  P  Q  S  N  E  L  L  R  D  F  E  V  T  L  L  Q  M  F  G  L
        310        320        330        340        350        360        370        380        390        400
TCCGCAAGCGGCCGCAGCCCAGTAAGGATGTGGTTCCCGCTTATATGCGCGACCTGTACAGGCTTCAGTCAGCGGAGGAGGAGGATGAACTGCACGA
  R  K  R  P  Q  P  S  K  D  V  V  P  A  Y  M  R  D  L  Y  R  L  Q  S  A  E  E  E  D  E  L  H  D
        410        420        430        440        450        460        470        480        490        500
TATCAGCATGGAGTACCCCGAGACACCCACCAGCCGCCAACACCGTGAGGAGCTTCCATCACGAGGAGAACATTTGGAGAATCTACCAGGCACAGAAGAA
  I  S  M  E  Y  P  E  T  P  T  S  R  A  N  T  V  R  S  F  H  H  E  E  H  L  E  N  L  P  G  T  E  E
        510        520        530        540        550        560        570        580        590        600
AATGGAAATTTCCGTTTGTGTTCAACCTCAGCAGCATTCCAGAGAGAATGAGGTGATTTCTTCAGCAGAACTGAGACTCTATAGAGAACAAATAGACCATG
  N  G  N  F  R  F  V  F  N  L  S  S  I  P  E  N  E  V  I  S  S  A  E  L  R  L  Y  R  E  Q  I  D  H  G
        610        620        630        640        650        660        670        680        690        700
GTCCAGGCGTGGGATGAGGGTTTCCACCGGATAAATATATGAAGTTATGAAACCCATCACAGCAAACGGACACATGATAAATAGGCTGCTGGACACGAG
  P  A  W  D  E  G  F  H  R  I  N  I  Y  E  V  M  K  P  I  T  A  N  G  H  M  I  N  R  L  L  D  T  R
        710        720        730        740        750        760        770        780        790        800
GTAATCCACCACAATGTGACACAGTGGGAAAGTTTTGATGTAAGCCCCTGCAATTATGAGGTGGACCCTGGATAAACAGATAAACCATGGGCTTGCCATT
  V  I  H  H  N  V  T  Q  W  E  S  F  D  V  S  P  A  I  M  R  W  T  L  D  K  Q  I  N  H  G  L  A  I
```

Fig.2(7)-2
pxbr23 (BMP2B)

```
         810       820       830       840       850       860       870       880       890       900
GAGGTCATTCACCTCAACCAACAAACTTATCAGGGAAGCATGTAAGGATCTTTATTACCTCAAAAGGATGCAGACTGGTCACAGATGA
 E  V  I  H  L  N  Q  T  K  T  Y  Q  G  K  H  V  R  I  S  R  S  L  L  P  Q  K  D  A  D  W  S  Q  M  R
         910       920       930       940       950       960       970       980       990       1000
GACCACTTTTAATTACATTCAGCCATGATGGCAGGGGGCATGCACTGACTAGGAGGTCAAAAGAAGTCCAAAACAGCAGAGACCCCGTAAAAAAATAA
 P  L  L  I  T  F  S  H  D  G  R  G  H  A  L  T  R  R  S  K  R  S  P  K  Q  Q  R  P  K  K  N  K
         1010      1020      1030      1040      1050      1060      1070      1080      1090      1100
ACACTGCCGGAGACATTCTTTTATGTGGATTTCAGCGATGTGGGCTGGAATGATTGGATTGTGGCACCTCCTGGATACCAGGCCTTTACTGCCATGGA
 H  C  R  R  H  S  L  Y  V  D  F  S  D  V  G  W  N  D  W  I  V  A  P  P  G  Y  Q  A  F  Y  C  H  G
         1110      1120      1130      1140      1150      1160      1170      1180      1190      1200
GATTGTCCATTCCCTGGCTGATCACCTAAACTCTAACCATGCTATTGTACAAATCTGTTAACTCAAGCATCCAAAAGCATGCT
 D  C  P  F  P  L  A  D  H  L  N  S  T  N  H  A  I  V  Q  I  L  V  N  S  V  N  S  S  I  P  K  A  C  C
         1210      1220      1230      1240      1250      1260      1270      1280      1290      1300
GCGTCCCCACAGAACTGAGTGCTATCTCCATGCTTTATTTGGATGAATATGACAAAGTCGTCTTAAAAACTACCAGGAGATGGTGGTGGAAGGGTGTGG
 V  P  T  E  L  S  A  I  S  M  L  Y  L  D  E  Y  D  K  V  V  L  K  N  Y  Q  E  M  V  V  E  G  C  G
         1310      1320      1330      1340      1350      1360      1370      1380      1390      1400
GTGCCGTTGAGTCTGAGATCCAAACAAAGACTGTTAACGGCTGACTTCTTCCACTGAACATTCACCTTGACCTTATTTATGACTTTTATGTGTAAAT
 C  R  *
         1410      1420      1430      1440      1450      1460      1470      1480      1490      1500
GTTTTTTGACAATATGATCATATATTTGACAAATATATTTATAACTACGTATTAAAAGAAAAAAAATAAGTCATTATTTTAAACATAA
         1510      1520      1530      1540      1550
AAAAAAAAAAAAAAAAAAAAAAAAAAAAAAAAAAAAAAAAAAAAAAAAAAACGGAATTC
```

Fig.2(8)-1
pxbr41(Vgr1)

```
         10         20         30         40         50         60         70         80         90        100
GAATTCCGATATGGAATGTAAAAATACTGGTGAATTATGGGAAGTCCGACAGACCACTAACTTCAGCATCTTATCTTTGACAAAATGAATGCTTTGAC
                                                                                        M  N  A  L  T 110        120        130        140        150        160        170        180        190        200
AGTAAAGAGAAGATTGCCTGTGCTGCTTTTCTTTTTCACATTTCACTGAGTTCCATCTCGTCAAATACAATATTGGAGAATGATTCCACTCTAGTTTT
 V  K  R  R  L  P  V  L  L  F  H  I  S  L  S  S  I  S  S  N  T  I  L  E  N  D  F  H  S  S  F 210        220        230        240        250        260        270        280        290        300
GTCCAGAGAAGACTAAAGGCCACGAACGCAGAGAGATTCAAAAAGAGATCTTGACTATTTTAGGTTGCAACACAGACCAAGGCCATATTTACCGGAGA
 V  Q  R  R  L  K  G  H  E  R  R  E  I  Q  K  E  I  L  T  I  L  G  L  Q  H  R  P  R  P  Y  L  P  E  K 310        320        330        340        350        360        370        380        390        400
AAAGAAGTCTGCACCATTATTCATGATGGATTTATACAATGCAGTAAATATTGAAGAGATGCATGCTGAAGATGTTCCTACAGCAATAAGCCGATCTC
 K  K  S  A  P  L  F  M  M  D  L  Y  N  A  V  N  I  E  E  M  H  A  E  D  V  S  Y  S  N  K  P  I  S 410        420        430        440        450        460        470        480        490        500
CCTAAATGAAGCTTTTCACTGGCCACTGACCAAGAGAATGGCTTTCTTGCACATGCCGACACAGTTGAGTTTTGCTAATTTAGTTGACAATGACAAC
 L  N  E  A  F  S  L  A  T  D  Q  E  N  G  F  L  A  H  A  D  T  V  M  S  F  A  N  L  V  D  N  D  N 510        520        530        540        550        560        570        580        590        600
GAATTGCATAAAAACTCCTATCGCCAAAATTCAAGTTGATCTAACTGATATCCCACTTGGAGATGAACTGACAGCCGCTGAATTTCGAATTTATAAAG
 E  L  H  K  N  S  Y  R  Q  K  F  K  F  D  L  T  D  I  P  L  G  D  E  L  T  A  A  E  F  R  I  Y  K  D 610        620        630        640        650        660        670        680        690        700
ATTATGTACAAAATAACGAGACATACCAGGTCACCATCTACCAGGTGCTTAAGAAGCAAGCCGACAAAGATCCTTATCTTTTCCAGGTAGACTCAAGAAC
 Y  V  Q  N  N  E  T  Y  Q  V  T  I  Y  Q  V  L  K  K  Q  A  D  K  D  P  Y  L  F  Q  V  D  S  R  T 710        720        730        740        750        760        770        780        790        800
CATCTGGGGCACAGAAAAGGGATGGCTGACGTTTGATATTACTGCAACTGGTAATCACTGGGTGATGAACCCACATTACAACCTTGGATTGCAGTTATCA
 I  W  G  T  E  K  G  W  L  T  F  D  I  T  A  T  G  N  H  W  V  M  N  P  H  Y  N  L  G  L  Q  L  S
```

Fig.2(8)-2
pxbr41(Vgr1)

```
        810       820       830       840       850       860       870       880       890       900
GTAGAGAGTATGGATATGCAAATGTTAATCCCAGGCTTGTGGGCCTTGTGTTGGAAAGAATGGTCCTCAAGACAAACAGCCATTTATGGTGGCATTCTTTA
 V  E  S  M  D  M  Q  N  V  N  P  R  L  V  G  L  V  G  K  N  G  P  Q  D  K  Q  P  F  M  V  A  F  F  K 910       920       930       940       950       960       970       980       990      1000
AGACCTCAGATATCCATCTCCGGCAGTGTTCGATCTGTTCGATCTACTAGCAATAAGCACTGGAATCAGGAAAGAGCAAGACCTACAAGGAGCAAGATAATTTACCTCC
 T  S  D  I  H  L  R  S  V  R  S  T  S  N  K  H  W  N  Q  E  R  A  K  T  Y  K  E  Q  D  N  L  P  P 1010      1020      1030      1040      1050      1060      1070      1080      1090      1100
AGCAAATATTACTGATGGCATCATGCCCCCTGGAAAACGTCGTTTTTTAAAGCAAGCTTGCAAGAAACATGAACTGTTGTTAAGTTTCCGCGATCTTGGT
 A  N  I  T  D  G  I  M  P  P  G  K  R  R  F  L  K  Q  A  C  K  K  H  E  L  F  V  S  F  R  D  L  G 1110      1120      1130      1140      1150      1160      1170      1180      1190      1200
TGGCAAGACTGGATAATTGCACCTGAAGGATATGCTGCCTACTATTGTGATGGAGAATGTGCTTTCCCACTTAACTCTTCATGAATGCCACAAACCATG
 W  Q  D  W  I  A  P  E  G  Y  A  A  Y  Y  C  D  G  E  C  A  F  P  L  N  S  F  M  N  A  T  N  H  A 1210      1220      1230      1240      1250      1260      1270      1280      1290      1300
CCATTGTACAAACGTTGGTACATTTCATTAACCCAGAGACTGTCCCTAAGCCATGCTGTGCACCAACTCAGCTCAATGGTATTCTGTTTTATACTTTGA
 I  V  Q  T  L  V  H  F  I  N  P  E  T  V  P  K  P  C  C  A  P  T  Q  L  N  G  I  S  V  L  Y  F  D 1310      1320      1330      1340      1350      1360      1370      1380      1390      1400
TGACAGTGCCAATGTTCTTATATTAAAGAAATACAAAAATATGGTGGTTCAAGCCTGTGGTTGCCATTGACAATAGCAGTTATTCTGTTTTTAACAGTCATTT
 D  S  A  N  V  L  K  K  Y  K  N  M  V  V  Q  A  C  G  C  H  *

1410      1420      1430      1440      1450      1460      1470      1480      1490      1500
TAATGGTATTGTCCTTATCGTTTATTTAAAGTAGAGATACTTGACCATCACACTTAAAAAAATGCATTGTACACCTTAACGGATGAAAAGATTTGTTT

1510
TTGCATGATTTCGGAATTC
```

Fig. 3

```
βA          ARQSEDIPIRRRRR--GLECDGKVNICCKKQFFVSFKDIGWNDWIIAPSGYIIANYCEGECPSHIAG....
B9(I)       ..TDE.....KK.-..........S......H.Y..........S......P....D.....
M3(II)      AK-VHEQS.HATK.--S.N..QNS.L..R.DYY.D...........K.E..QI...M.L..M...
βB          ..LGDSR-..I..K..-.......RTSL..RQ...ID.RL...........T..YG.....S...AYL..
BMP2A       K.EKRQAK.KQ..K..-----,------,SS-,KRIIPLY.D.S.V........V..P....F...H...FPL.D
C4(III)     K..KRQAR.KQ..K..-----,------,SS-,RRIIPLY.D.S.V........V..P....F...H...FPL.D
DPPC        ...-HARRPT...KN----H-----DDT-,RRHSLY.D.S.V..DD.V..L..D.Y..H.K..FPL.D
Vg1         TLNPLRCKRP...K.SYSKLPFTAS....K.RHLY.E...V..QN.V...Q..M....Y...YPLTE
A4(IV)      R.KRRAPLST.--QGKRPNKNS.AR-..S..PLH.N..M..D......LE.E.YH...L.EFPLRS
A5(V)       R.WKRTTLPT.TNNGK.HAKKS.TR-..S..PLL.N..EL..D......LD.E.YH...V.DFPLRS
CONSENSUSE  .........................C.......F...GW..W...P..Y....C.G.C........

βA          TSGSSLSFHSTVINHYRMRGHSPFANLKSCCVPTKLRPMSMLYYDDGQNIIKKDIQNMIVEECGCS
B9(I)       .T..............Q..L..Q...TSI........S...A.....................
M3(II)      AP.TAA...T..L.LIK--ANNIQTAVN......R..L....F.RNN.VL.T..AD....A....
βB          VP..AS...TA.V..Q.....LN.-GPVN....I....SS......F..EY..V.R.VP......A
BMP2A       H---LNSTN.AI.QTLVN--SVNSK-IP.A.....E.SAI......L.ENEKVVL.NY.D.V..G...R
C4(III)     H---LNSTN.AI.QTLVN--SVNTN-IP.A.....E.SAI......L.ENEKVVL.NY.D.V..G...R
DPPC        H---FNSTN.AV.QTLVN-NMNPGK-VP.A.....QLDSVA..LN.QSTVVL.NY.E.T.VG...R
Vg1         I---LNG.N.AILQTLVH--SIE.EDIPLP.....MS.I...F..NND.VVLRHYE..A.D....R
CONSENSUS   .........................CC.P......ML..D.............M.V..CGC.
         ***
```

Fig.4-1
(VI) BMP2A

```
            M V A G I H S L L L Q F Y Q I
      L L S G C T G L V P E E G K R K Y S E S T
      R S S P Q Q S Q Q V L D Q F E L R L L N M
      F G L K R R P T P G K N V V I P P Y M L D
      L Y H L H S A Q L A D D Q G S S E V D Y H
      M E R A A S R A N T V R S F H H E E S M E
      E I P E S G E K T I Q R F F F N L S S I P
      D E E L V T S S E L R I F R E Q V Q E P F
      K T D G S K L H R I N I Y D I V K P A A A
      A S R G P V V R L L D T R L I H H N E S K
      W E S F D V T P A I T R W I A H K Q P N H
      G F V V E V T H L D N D T N V P K R H V R
      I S R S L T L D K G H W P R I R P L L V T
      F S H D G K G H A L H K R Q K R Q A R H K
      Q R K R L K S S C R R H P L Y V D F S D V
      G W N D W I V A P P G Y H A F Y C H G E C
      P F P L A D H L N S T N H A I V Q T L V N
      S V N T N I P K A C C V P T E L S A I S M
      L Y L D E N E K V V L K N Y Q D M V V E G
      C G C R *
```

Fig.4-2
(VII) BMP2B

```
        M  I  P  G  N  R  M  L  M  V  I  L  L  S  Q  V  L  L  G  G
  T  N  Y  A  S  L  I  P  D  T  G  K  K  K  V  A  A  D  I  Q  G
  G  G  R  R  S  P  Q  S  N  E  L  L  R  D  F  E  V  T  L  L  Q
  M  F  G  L  R  K  R  P  Q  P  S  K  D  V  V  V  P  A  Y  M  R
  D  L  Y  R  L  Q  S  A  E  E  E  D  E  L  H  D  I  S  M  E  Y
  P  E  T  P  T  S  R  A  N  T  V  R  S  F  H  H  E  E  H  L  E
  N  L  P  G  T  E  E  N  G  N  F  R  F  V  F  N  L  S  S  I  P
  E  N  E  V  I  S  S  A  E  L  R  L  Y  R  E  Q  I  D  H  G  P
  A  W  D  E  G  F  H  R  I  N  I  Y  E  V  M  K  P  I  T  A  N
  G  H  M  I  N  R  L  L  D  T  R  V  I  H  H  N  V  T  Q  W  E
  S  F  D  V  S  P  A  I  M  R  W  T  L  D  K  Q  I  N  H  G  L
  A  I  E  V  I  H  L  N  Q  T  K  T  Y  Q  G  K  H  V  R  I  S
  R  S  L  L  P  Q  K  D  A  D  W  S  Q  M  R  P  L  L  I  T  F
  S  H  D  G  R  G  H  A  L  T  R  R  S  K  R  S  P  K  Q  Q  R
  P  R  K  K  N  K  H  C  R  R  H  S  L  Y  V  D  F  S  D  V  G
  W  N  D  W  I  V  A  P  P  G  Y  Q  A  F  Y  C  H  G  D  C  P
  F  P  L  A  D  H  L  N  S  T  N  H  A  I  V  Q  T  L  V  N  S
  V  N  S  S  I  P  K  A  C  C  V  P  T  E  L  S  A  I  S  M  L
  Y  L  D  E  Y  D  K  V  V  L  K  N  Y  Q  E  M  V  V  E  G  C
  G  C  R  *
```

```
                              Fig.4-3
                           (VIII) (Vgr1)
                                                M  N  A  L  T
        V  K  R  R  L  P  V  L  L  F  L  F  H  I  S  L  S  S  I  S  S
        N  T  I  L  E  N  D  F  H  S  S  F  V  Q  R  R  L  K  G  H  E
        R  R  E  I  Q  K  E  I  L  T  I  L  G  L  Q  H  R  P  R  P  Y
        L  P  E  K  K  K  S  A  P  L  F  M  M  D  L  Y  N  A  V  N  I
        E  E  M  H  A  E  D  V  S  Y  S  N  K  P  I  S  L  N  E  A  F
        S  L  A  T  D  Q  E  N  G  F  L  A  H  A  D  T  V  M  S  F  A
        N  L  V  D  N  D  N  E  L  H  K  N  S  Y  R  Q  K  F  K  F  D
        L  T  D  I  P  L  G  D  E  L  T  A  A  E  F  R  I  Y  K  D  Y
        V  Q  N  N  E  T  Y  Q  V  T  I  Y  Q  V  L  K  K  Q  A  D  K
        D  P  Y  L  F  Q  V  D  S  R  T  I  W  G  T  E  K  G  W  L  T
        F  D  I  T  A  T  G  N  H  W  V  M  N  P  H  Y  N  L  G  L  Q
        L  S  V  E  S  M  D  M  Q  N  V  N  P  R  L  V  G  L  V  G  K
        N  G  P  Q  D  K  Q  P  F  M  V  A  F  F  K  T  S  D  I  H  L
        R  S  V  R  S  T  S  N  K  H  W  N  Q  E  R  A  K  T  Y  K  E
        Q  D  N  L  P  P  A  N  I  T  D  G  I  M  P  P  G  K  R  R  F
        L  K  Q  A  C  K  K  H  E  L  F  V  S  F  R  D  L  G  W  Q  D
        W  I  I  A  P  E  G  Y  A  A  Y  Y  C  D  G  E  C  A  F  P  L
        N  S  F  M  N  A  T  N  H  A  I  V  Q  T  L  V  H  F  I  N  P
        E  T  V  P  K  P  C  C  A  P  T  Q  L  N  G  I  S  V  L  Y  F
        D  D  S  A  N  V  I  L  K  K  Y  K  N  M  V  V  Q  A  C  G  C
        H  *
```

XENOPUS LAEVIS BONE MORPHOGENETIC PROTEINS AND USE THEREOF

This is a continuation of application Ser. No. 07/577,892 filed on Sep. 5, 1990, now abandoned.

BACKGROUND OF THE INVENTION

The present invention relates to a DNA containing a DNA segment coding for a *Xenopus laevis* bone morphogenetic protein analogous to a bone morphogenetic protein (hereinafter referred to as BMP), a precursor protein (or a precursor polypeptide) and a mature protein (or a mature polypeptide) of the *Xenopus laevis* BMP, and a method for preparing the precursor protein and the mature protein.

In this specification, the term "precursor protein" includes a protein which includes an amino acid sequence of a mature peptide *Xenopus Laevis* BMP and has all or a portion of an amino acid sequence coded with a *Xenopus laevis* BMP DNA segment at the N-terminus, the C-terminus or both termini thereof.

Recently, it has been revealed that transforming growth factor-beta (TGF-beta, TGF-β) having a bone morphogenetic activity not only controls cell proliferation, but also has various biological activities such as control of cell differentiation. In particular, the bone morphogenesis-promoting activity of TGF-β has been noted, and attempts have been made to use TGF for treatment of fractures and osteoporosis, making use of the cartilage-bone induction activity thereof [M. Noda et al., *J. Endocrinology* 124, 2991–2994 (1989); M. E. Joyce et al., *J. Bone Mineral Res.* 4, S-259 (1989); and S. M. Seyedin et al., *J. Biol. Chem.* 281, 5693–5695 (1986)]. More recently, however, four kinds of bone morphogenetic proteins (BMPs) which are different from one another in molecular structure have been identified as a factor promoting morphogenesis of bones and cartilages. Of these four kinds, human BMP-1, human BMP-2A, human BMP-2B and human BMP-3 are novel peptides, though they are very similar in structure to TGF-β, and there has been a report that they induce morphogenesis of bones and cartilages when subcutaneously or intramuscularly implanted in animals [J. M. Wozney et al., *Science* 242, 1528–1534 (1989)].

The above peptides having bone morphogenetic activity are isolated and purified from bones in which the peptides are considered to be localized, or from human osteosarcoma cells (U2-OS) which are thought to produce the peptides. However, such a method has problems because the procedure is complicated and the desired peptides are obtained only in small amounts.

SUMMARY OF THE INVENTION

Important contributions will be made to future studies and medical treatment, if a similar peptide having the bone morphogenetic activity can be collected from *Xenopus laevis* and further prepared by recombinant technique. As a result, the following information was obtained, thus arriving at the present invention.

Namely, the present inventors first succeeded in cloning five kinds of DNA coding for BMP-2A and related DNAs (*Xenopus laevis* BMPs) and subsequently three kinds of complementary DNAs, eight kinds of DNAs in total, by using a complementary DNA of a rat inhibin βA chain equally belonging to the TGF-βfamily as a probe. Further, the present inventors identified portions of the bases of the DNAs, clarified the amino acid sequences (see formulae (1), (2), (3), (4) and (5) of FIG. 2 and formulae (6), (7) and (8) of FIG. 4) of the *Xenopus laevis* BMPs (referred to as B9, M3, C4, A4, A5,Xbr22, Xbr23 and Xbr41), and succeeded in pioneering their mass production by recombinant technique.

In accordance with the present invention, there are provided (1) a *Xenopus laevis* BMP, (2) a DNA comprising a DNA segment coding for the *Xenopus laevis* BMP, (3) a transformant bearing the DNA containing the DNA segment coding for the *Xenopus laevis* BMP and (4) a method for preparing the *Xenopus laevis* BMP which comprises culturing the transformant described in (3), producing and accumulating a protein in a culture and collecting the protein thus obtained.

BRIEF DESCRIPTION OF THE DRAWINGS

FIGS. 2(1) to 2(8) show nucleotide sequences of the DNA segments of *Xenopus laevis* BMPs, B9, M3, C4, A4, A5, BMP-2A, BMP-2B and Vgr-1, respectively, and the amino acid sequences deduced therefrom;

FIG. 3 shows amino acid sequences of the *Xenopus laevis* BMPs deduced from the nucleotide sequences of the DNA segments shown in FIGS. 2(1) to 2(5), comparing them with the amino acid sequences of known proteins having a bone morphogenetic activity; and FIG. 4 shows amino acid sequences of the *Xenopus laevis* BMPs deduced from the nucleotide sequences of the cDNA segments shown in FIGS. 2(6) to 2(8).

DESCRIPTION OF THE PREFERRED EMBODIMENTS

Figure 1:
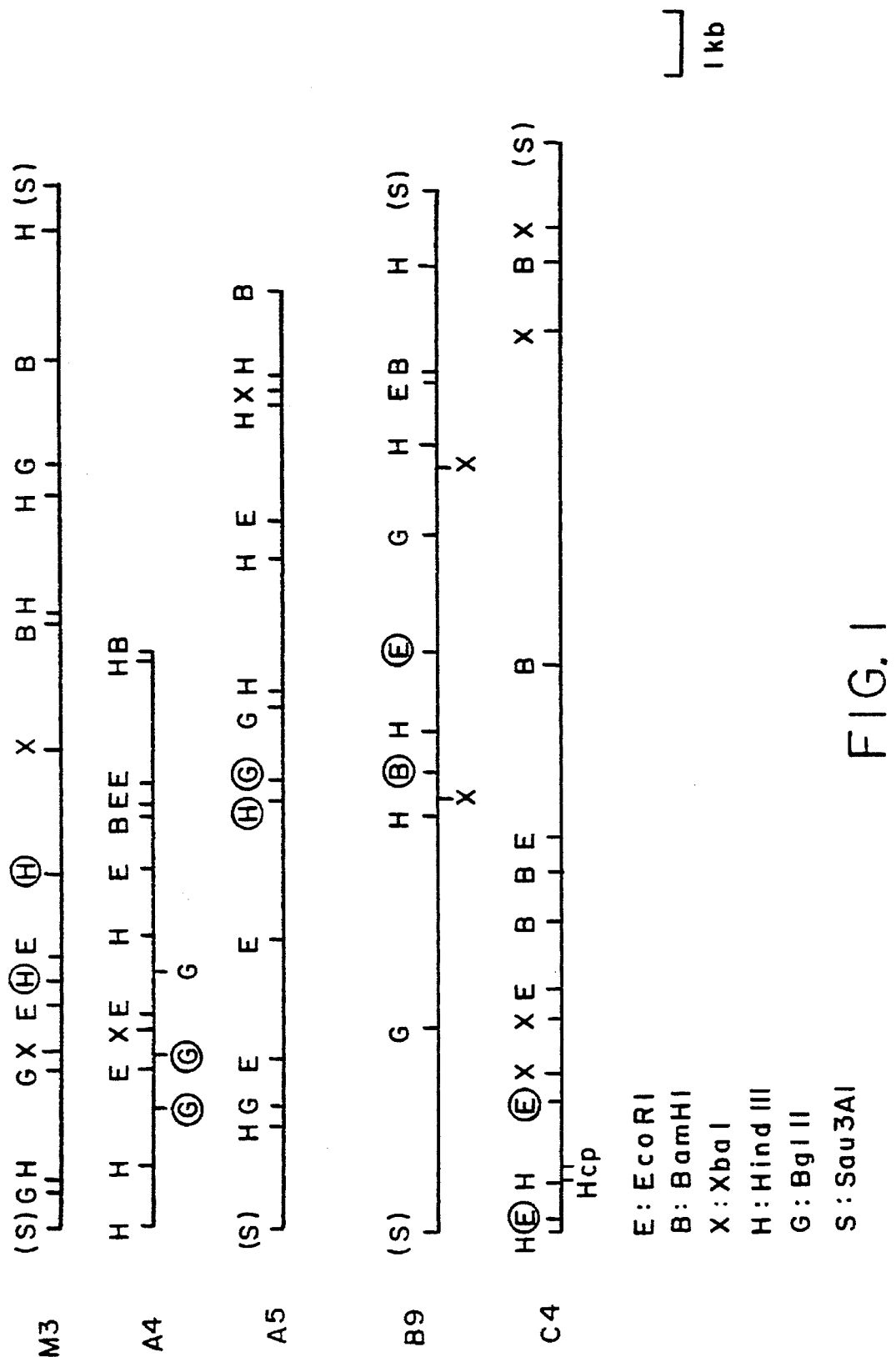
FIG. 1 shows simplified restriction enzyme maps of DNA sequences containing *Xenopus laevis* BMP precursors or mature peptide DNA segments.

The mature *Xenopus laevis* BMP of C4, one of the *Xenopus laevis* BMPs, of the present invention, which has a relationship to TGF-β and is a peptide consisting of 98 or 114 amino acid residues, has an amino acid sequence represented by Nos. 6 to 119 or Nos. 22 to 119 of formula (III) shown in FIG. 3. The molecular weight thereof is calculated at about 25,000, excepting sugar chains, when a dimer is formed.

The amino acid sequence of this peptide is different from that reported by Wozney et al. in 3 or 4 amino acid residues per molecule.

FIG. 3 shows amino acid sequences of five kinds of novel *Xenopus laevis* BMPs obtained in the present invention, comparing them with the amino acid sequences of known proteins having a bone morphogenetic activity. In these amino acid sequences, the same amino acid residue as with βA is represented by ".", and an amino acid residue different from that of βA is represented by one letter symbol based on βA. CONSENSUS shown in FIG. 3 indicates amino acid residues common to all the BMPs shown in FIG. 3. The illustration of CONSENSUS results in introduction of gaps "-" in the formulae in FIG. 3. Accordingly, the number representing the precursor and mature protein portions is counted excluding these lacking portions.

FIG. 4 shows amino acid sequences of three kinds of novel *Xenopus laevis* BMPs deduced from cDNAs, subsequently discovered by the present inventors.

For DNA sequences, the DNA segments coding for the *Xenopus laevis* BMPs of the present invention correspond to the nucleotide sequences of formulae (1) to (8) (corresponding to B9, M3, C4, A4, A5, Xbr22, Xbr23 and Xbr41, respectively) shown in FIG. 2 or are portions thereof. Any functional portion can be used so long as bone morphogenetic activity is not lost. Wozney et al. reports the amino acid sequences, but does not elucidate the nucleotide sequences. As used herein the term correspond permits conservative additions, deletions and substitutions. Preferably, the DNA segments coding for the BMPs of the present invention have the nucleotide sequences of formulae (1) to (8).

With respect to the portion relating to the mature BMPs [the amino acid sequence represented by Nos. 15 to 130 of formula (I) shown in FIG. 3, the amino acid sequence represented by Nos. 14 to 127 of formula (II) shown in FIG. 3, the amino acid sequence represented by Nos. 6 to 119 or Nos. 22 to 119 of formula (III) shown in FIG. 3, the amino acid sequence represented by Nos. 6 to 63 of formula (IV) shown in FIG. 3, the amino acid sequence represented by Nos. 6 to 65 of formula (V) shown in FIG. 3, the amino acid sequence represented by Nos. 282 to 398 or Nos. 298 to 398 of formula (VI) shown in FIG. 4, the amino acid sequence represented by Nos. 288 to 401 or Nos. 304 to 401 of formula (VII) shown in FIG. 4, or the amino acid sequence represented by Nos. 328 to 426 of formula (VIII) shown in FIG. 4], the DNA sequences of the present invention differ from the DNA sequence of TGF-β, and therefore are novel.

As the DNA sequences coding for the BMP mature peptides of the present invention, any DNA sequences may be used as long as they contain nucleotide sequences coding for the amino acid sequences of the BMP mature peptides. For example, DNA sequences corresponding to the nucleotide sequences represented by formulae (1) to (8) or portions thereof are preferably used. More preferably the DNA sequences contain the nucleotide sequences represented by formulae (1) to (8).

The nucleotide sequences represented by formulae (1) to (8) are the *Xenopus laevis* BMP DNA sequences obtained in the present invention. Examples of the nucleotides coding for the *Xenopus laevis* BMP amino acid sequences represented by formulae (I) to (VIII) include Nos. 693 to 1040 of formula (1), Nos. 134 to 475 of formula (2), Nos. 435 to 728 formula (3), Nos. 183 to 356 of formula (4), Nos. 149 to 328 of formula (5), Nos. 249 to 1442 of formula (6), Nos. 104 to 1306 of formula (7) and Nos. 86 to 1363 of formula (8).

An expression vector having the DNA sequence containing the nucleotide sequence coding for the BMP of the present invention can be prepared, for example, by the following process:

(a) Messenger RNA (mRNA) is isolated from BMP-producing cells.

(b) Single stranded complementary DNA (cDNA) is synthesized from the mRNA, followed by synthesis of double stranded DNA.

(c) The complementary DNA is introduced in a cloning vector such as a phage or a plasmid.

(d) Host cells are transformed with the recombinant phage or plasmid thus obtained.

(e) After cultivation of the transformant thus obtained, the plasmid or the phage containing the desired DNA is isolated from the transformant by an appropriate method such as hybridization with a DNA probe coding for a portion of the BMP or immunoassay using an anti-BMP antibody.

(f) The desired cloned DNA sequence is cut out from the recombinant DNA.

(g) The cloned DNA sequence or a portion thereof is ligated downstream from a promoter in the expression vector.

The mRNAs coding for the BMPs can be obtained from various BMP-producing cells such as ROS cells.

Methods for preparing the mRNAs from the BMP-producing cells include the guanidine thiocyanate method [J. M. Chirgwin et al., *Bio-chemistry* 18, 5294 (1979)].

Using the mRNA thus obtained as a template, cDNA is synthesized by use of reverse transcriptase, for example, in accordance with the method of H. Okayama et al. [*Molecular and Cellular Biology* 2, 161 (1979); ibid. 3, 280 (1983)]. The cDNA thus obtained is introduced into the plasmid.

The plasmids into which the cDNA is introduced include, for example, pBR322 [*Gene* 2, 95 (1977)], pBR325 [*Gene* 4, 121 (1978)], pUC12 [*Gene* 19, 259 (1982)] and pUC13 [*Gene* 19, 259 (1982)], each derived from *Escherichia coli*, and pUB110 derived from *Bacillus subtilis* [*Biochemical and Biophysical Research Communication* 112, 678 (1983)]. However, any other plasmids can be used as long as they are replicable and growable in the host cells. Examples of the phage vectors into which the cDNA may be introduced include λgt11 [R. Young and R. Davis, *Proc. Natl. Acad. Sci. U.S.A.* 80, 1194 (1983)]. However, any other phage vectors can be used as long as they are growable, in the host cells.

Methods for introducing the cDNA in the plasmid include, for example, the method described in T. Maniatis et al., *Molecular Cloning*, Cold Spring Harbor Laboratory, p.239 (1982). Methods for introducing the cDNA in the phage vector include, for example, the method of T. V. Hyunh et al. [*DNA Cloning, A Practical Approach* 1, 49 (1985)].

The plasmid thus obtained is introduced into the appropriate host cell such as Escherichia and Bacillus.

Examples of Escherichia described above include *Escherichia coli* K12DH1 [*Proc. Natl. Acad. Sci. U.S.A.* 60, 160 (1968)], M103 [*Nucleic Acids Research* 9, 309 (1981)], JA221 [*Journal of Molecular Biology* 120, 517 (1978)], HB101 [*Journal of Molecular Biology* 41, 459 (1969)] and C600 [*Genetics* 39, 440 (1954)].

Examples of Bacillus described above include *Bacillus subtilis* MI114 [*Gene* 24, 255 (1983)] and 207–21 [*Journal of Biochemistry* 95, 87 (1984)].

Methods for transforming the host cell with the plasmid include, for example, the calcium chloride method or the calcium chloride/rubidium chloride method described in T. Maniatis et al., *Molecular Cloning*, Cold Spring harbor Laboratory, p.249 (1982).

When the phage vector is used, for example, the phage vector can be transduced into multiplied *Escherichia coli*, using the in vitro packaging method.

*Xenopus laevis* cDNA libraries containing *Xenopus laevis* BMP cDNA can be obtained by numerous techniques well known in the art including purchasing them from the market, though obtainable by the methods described above. For example, the cDNA library of *Xenopus laevis* is available from Clontech Laboratories, Inc., U.S.A.

Methods for cloning the *Xenopus laevis* BMP DNA from the *Xenopus laevis* DNA library include, for example, the plaque hybridization method using phage vector λcharon 28A and rat inhibin (activin) βA cDNA as probes [T. Maniatis et al., *Molecular Cloning*, Cold Spring Harbor Laboratory, (1982)].

The *Xenopus laevis* BMP DNA thus cloned is subcloned in plasmids such as pBR322, pUC12, pUC13, pUC19, pUC118 and pUC119 to obtain the *Xenopus laevis* BMP DNA, if necessary.

The nucleotide sequence of the DNA sequence thus obtained is determined, for example, by the Maxam-Gilbert method [A. M. Maxam and W. Gilbert, *Proc. Natl. Acad. Sci. U.S.A.* 74, 560 (1977)]or the dideoxy method [J. Messing et al., *Nucleic Acids Research* 9, 309 (1981)], and the existence of the *Xenopus laevis* BMP DNA is confirmed in comparison with the known amino acid sequence.

As described above, the DNA sequence [*Xenopus laevis* BMP DNAs represented by formulae (1) to (8)] coding for the *Xenopus laevis* BMPs are obtained.

FIG. 1 shows the restriction enzyme fragment maps of the DNA sequences containing the DNA segments coding for the *Xenopus laevis* BMPs obtained in Example 1 described below. FIG. 2 shows the nucleotide sequences represented by formulae (1) to (8) of the DNA sequences as determined by the dideoxy method, and FIGS. 3 and 4 show the amino acid sequences represented by formulae (I) to (V) and formulae (VI) to (VIII), respectively, which were ascertained form the above nucleotide sequences.

The DNA sequence coding for the *Xenopus laevis* BMP cloned as described above can be used as it is, or after digestion with a restriction enzyme if desired, depending on the intended use.

A region intended to be expressed is cut out from the cloned DNA and ligated downstream from the promoter in a vehicle (vector) suitable for expression, whereby the expression vector can be obtained.

The DNA sequence has ATG as a translation initiating codon at the 5'-terminus thereof and may have TAA, TGA or TAG as a translation terminating codon at the 3'-terminus. The translation initiating codon and translation terminating codon may be added by use of an appropriate synthetic DNA adaptor. The promoter is further ligated in the upstream thereof for the purpose of expressing the DNA sequence.

Examples of the vectors include the above plasmids derived from *E. coli* such as pBR322, pBR325, pUC12 and pUC13, the plasmide derived from *B. subtilis* such as pUB110, pTP5 and pC194, plasmids derived from yeast such as pSH19 and pSH15, bacteriophage such as λphage, and animal viruses such as retroviruses and vaccinia viruses.

As the promoters used in the present invention, any promoters are appropriate as long as they are suitable for expression in the host cells selected for the gene expression. When the host cell used for transformation is Escherichia, it is preferable that a trp promoter, a lac promoter, a recA promoter, a λPL promoter, a 1pp promoter, etc. are used. When the host cell is Bacillus, it is preferable that a PHO5 promoter, a PGK promoter, a GAP promoter, an ADH promoter etc. are used. In particular, it is preferable that the host cell is Escherichia and the promoter is the trp promoter or the λPL promoter.

When the host cell is an animal cell, an SV-40 derived promoter, a retrovirus promoter, a metallothionein promoter, a heat shock promoter, etc. are each usable.

An enhancer, a certain DNA sequence important for promoter activity in a cell, is also effectively used for expression.

By using the vector containing the DNA sequence coding for the *Xenopus laevis* BMP mature peptide thus constructed, the transformant is prepared.

The host cells include, for example, Escherichia, Bacillus, yeast and animal cells.

Specific examples of the above Escherichia and Bacillus include strains similar to those described above.

Examples of the above yeast include *Saccharomyces cerevisiae* AH22, AH22R⁻, NA87–11A and DKD-5D.

Examples of animal cells include monkey cell COS-7, Vero, Chinese hamster cell (CHO), mouse L cell and human FL cell.

The transformation of the above Escherichia is carried out, for example, according to the method described in *Proc. Natl. Acad. Sci. U.S.A.* 69, 2110 (1972) or Gene 17, 107 (1982).

The transformation of the above Bacillus is conducted, for example, according to the method described in *Molecular & General Genetics* 168, 111 (1979).

The transformation of the yeast is carried out, for example, according to the method described in *Proc. Natl. Acad. Sci. U.S.A.* 75, 1929 (1978).

The transformation of the animal cells is carried out, for example, according to the method described in *Virology* 52, 456 (1973).

Thus, there is obtained the transformant transformed with the expression vector containing the DNA sequence coding for the *Xenopus laevis* BMP mature peptide.

When bacterial transformants are cultured, a liquid medium is particularly suitable as a medium used for culture. Carbon sources, nitrogen sources, inorganic compounds and others necessary for growth of the transformant are contained therein. Examples of the carbon sources include glucose, dextrin, soluble starch and sucrose. Examples of the nitrogen sources include inorganic or organic materials such as ammonium salts, nitrates, corn steep liquor, peptone, casein, meat extracts, soybean meal and potato extract solution. The inorganic compounds include, for example, calcium chloride, sodium dihydrogenphosphate and magnesium chloride. Yeast extract, vitamins, growth promoting factors and so on may be further added thereto.

The pH of the medium is preferably about 5 to 8.

As the medium used for cultivation of Escherichia, there is preferred, for example, M9 medium containing glucose and Casamino Acids (Miller, *Journal of Experiments in Molecular Genetics* 431–433, Cold Spring Harbor Laboratory, New York, 1972). In order to make the promoter act efficiently, a drug such as 3β-indolylacrylic acid may be added thereto if necessary.

When the host cell is Escherichia, the cultivation is usually carried out at about 15° to 43° C. for about 3 to 24 hours, with aeration or agitation if necessary.

When the host cell is Bacillus, the cultivation is usually carried out at about 30° to 40° C. for about 6 to 24 hours, with aeration or agitation if necessary.

When yeast transformants are cultured, there is used, for example, Burkholder minimum medium [K. L. Bostian et al., *Proc. Natl. Acad. Sci. U.S.A.* 77, 4505 (1980)] as the medium. The pH of the medium is preferably adjusted to about 5 to 8. The cultivation is usually carried out at about 20° to 35° C. for about 24 to 72 hours, with aeration or agitation if necessary.

When animal cell transformants are cultured, examples of the media include MEM medium containing about 5 to 20% fetal calf serum [*Science* 122, 501 (1952)], DMEM medium [*Virology* 8, 396 (1959)], RPMI1640 medium [*Journal of the American Medical Association* 199, 519 (1967)] and 199 medium [*Proceeding of the Society for the Biological Medicine* 73, 1 (1950)]. The pH is preferably about 6 to 8. The cultivation is usually carried out at about 30° to 40° C. for about 15 to 60 hours, with aeration or agitation if necessary.

The above *Xenopus laevis* BMP mature peptide can be isolated and purified from the culture described above, for example, by the following method.

When the *Xenopus laevis* BMP mature peptide is to be extracted from the cultured cells, the cells are collected by methods known in the art after cultivation. Then, the collected cells are suspended in an appropriate buffer solution and disrupted by ultrasonic treatment, lysozyme and/or freeze-thawing. Thereafter, a crude extracted solution of the *Xenopus laevis* BMP mature peptide is obtained by centrifugation or filtration. The buffer solution may contain a protein denaturant such as urea or guanidine hydrochloride, or a surface-active agent such as Triton X100.

When the *Xenopus laevis* BMP precursor protein or mature peptide is secreted in the culture solution, a supernatant is separated from the cells by methods known in the art after the conclusion of cultivation, and then collected.

The separation and purification of the *Xenopus laevis* BMP precursor protein or mature peptide contained in the culture supernatant or the extracted solution thus obtained can be performed by an appropriate combination of known separating and purifying methods. The known separating and purifying methods include methods utilizing solubility such as salt precipitation and solvent precipitation, methods mainly utilizing a difference in molecular weight such as dialysis, ultrafiltration, gel filtration and SDS-polyacrylamide gel electrophoresis, methods utilizing a difference in electric charge such as ion-exchange column chromatography, methods utilizing specific affinity such as affinity chromatography, methods utilizing a difference in hydrophobicity such as reverse phase high performance liquid chromatography and methods utilizing a difference in isoelectric point such as isoelectro-focusing electrophoresis. Methods using an antibody to a fused protein expressed by fusing a BMP complementary DNA or DNA with *E. coli*-derived DNA lacZ can also be used.

Illustrative examples of the methods for expressing the BMP in the present invention include methods in which genes are introduced into CHO cells to produce the BMP in large amounts as described in Wang et al., *Proc. Natl. Acad. Sci. U.S.A.* 807, 2220–2224 (1990).

The activity of the *Xenopus laevis* BMP precursor protein or mature peptide thus formed can be measured by an enzyme immunoassay using a specific antibody. If the products have a bone morphogenetic activity, this activity may also be measured as an index.

The cells, such as animal cells or *E. coli*, transinfected or transformed with the DNA sequences of the present invention allow large amounts of the *Xenopus laevis* BMP mature peptides to be produced. Hence, the production of these peptides can be advantageously achieved.

It has become clear that the *Xenopus laevis* BMP mature peptides prepared here promote the synthesis of proteoglycan which is a main component of a cartilage matrix, and the peptides can also be utilized for analysis of the mechanism of organism, particularly human bone-cartilage morphogenetic reaction, and as therapeutic agents for fracture or osteoporosis.

In such instances one would administer an effective amount of the protein to a mammal. An effective amount is the amount of protein needed to promote the synthesis of proteoglycan in cartilage cells. Typically, this ranges from 0.001 to 35 μg per kg/body weight. The precise amount for a particular purpose can readily be determined empirically by the person of ordinary skill in the art based upon the present disclosure.

When one uses the protein for therapeutic purpose care is taken to purify it and render it substantially free of bacterica and pyrogens. This can be done by standard methods.

When the BMPs are used as therapeutic agents for fracture or osteoporosis, they can be administered parenterally in the forms, of solutions, injections and ointments, solely or in combination with pharmaceutically acceptable additional components, such as vehicles, binders, dispersants, plasticizers or diluents.

The preferable administration forms include (1) administration of the agent to cutis surface near a diseased part, (2) injection of the agent into a diseased part, (3) discission of a diseased part followed by direct administration of the agent thereto. The preferable dose in fractue therapy for adult people is 0.1 to 2000 μg more, preferably 20 to 400 μg for adult people once a day. The preferable dose in osteoporosis for adult people is 0.1 to 200 μg once a day, for about one to 30 days. The concentration of the therapeutic agent is, preferably, 0.001 to 0.2% in the form of a solution, 0.001 to 0.2% in the form of an injections, and 0.0001 to 0.2% in the form of an ointment.

There have been described above in detail the cloning of the DNA sequences coding for the *Xenopus laevis* BMPs, the preparation of the expression vectors for the *Xenopus laevis* BMP mature peptides, the production of the transformants by using the transformants and their utility.

When nucleotides, amino acids and so on are indicated by the abbreviations in this specification and drawings, the abbreviations adopted by IUPAC-IUB Commission on Biochemical Nomenclature or commonly used in the art are employed. For example, the following abbreviations are used. When the amino acids are capable of existing as optical isomer, the L-forms are represented unless otherwise specified.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetraacetic acid
SDS: Sodium dodecyl sulfate
Gly or G: Glycine
Ala or A: Alanine
Val or V: Valine
Leu or L: Leucine
Ile or I: Isoleucine
Ser or S: Serine
Thr or T: Threonine
Cys of C: Cysteine
Met or M: Methionine
Glu or E: Glutamic acid
Asp or D: Aspartic acid
Lys or K: Lysine
Arg or R: Arginine
His or H: Histidine
Phe or F: Phenylalanine
Tyr or Y: Tyrosine
Trp or W: Tryptophan
Pro of P: Proline
Asn or N: Asparagine
Gln or Q: Glutamine With respect to the *Xenopus laevis* BMP mature peptides of the present invention, a portion of the amino acid sequence may be modified, namely there may be addition, elimination or substitution with other amino acids as long as the bone morphogenetic activity is not lost.

The present invention will hereinafter be described in detail with the following Examples. It is understood of course that these Examples are not intended to limit the scope of the invention.

Transformants *E. coli* HB101/pXar3 (coding for protein M3), *E. coli* HB101/pXar4 (coding for protein A4), *E. coli* HB101/pXar5 (coding for protein A5), *E. coli* HB101/pXar9 (coding for protein B9) and *E. coli* HB101/pXar14 (coding for protein C4) each obtained in Example 1 described below were deposited with the Institute for Fermentation, Osaka, Japan (IFO) under the accession numbers IFO 14928, IFO 14929, IFO 14930, IFO 14931 and IFO 14932, respectively, on Aug. 28, 1989. These transformants were also deposited with the Fermentation Research Institute, Agency of Industrial Science and Technology, Ministry of International Trade and Industry, Japan (FRI) under the Budapest Treaty under the accession numbers FERM BP 2578, FERM BP-2579, FERM BP-2580, FERM BP-2581 and FERM BP-2582, respectively, on Sep. 2, 1989.

The transformants *E. coli* HB101/pXbr22 (coding for *Xenopus laevis* BMP-2A), *E. coli* HB101/pXbr23 (coding for *Xenopus laevis* BMP-2B) and *E. coli* HB101/pXbr41 (coding for protein *Xenopus laevis* Vgr-1) each obtained in Example 2 described below were deposited with the Institute for Fermentation, Osaka, Japan (IFO) under the accession numbers IFO 15080, IFO 15081 and IFO 15082, respectively, on Aug. 10, 1990. These transformants were also deposited with the Fermentation Research Institute, Agency of Industrial Science and Technology, Ministry of International Trade and Industry, Japan (FRI) under the Budapest Treaty under the accession numbers FERM BP-3066, FERM BP-3065 and FERM BP-3067, respectively, on Aug. 16, 1990.

EXAMPLE 1

Preparation of *Xenopus laevis* Liver-Derived DNA Library
(1) Preparation of *Xenopus laevis* Chromosome DNA The liver (1 g) of *Xenopus laevis* was powdered in liquid nitrogen, and 10 m of buffer (1) [100 µg/ml proteinase K, 0.5% Sarkosil, 0.5M EDTA (pH 8.0)] was added thereto, followed by incubation at 50° C. for 2hours. The resulting DNA sample was treated with phenol, and then dialyzed against buffer (2) [10 mM EDTA, 10 mM NaCl, 50 mM Tris-HCl (pH 8.0)] to remove phenol. RNase was added thereto to a final concentration of 100 µg/ml, and the mixture was incubated at 37° C. for 3 hours, followed by phenol treatment twice. The aqueous layer was dialyzed against buffer (3) [1 mM EDTA, 10 mM Tris-HCl (pH 8.0)]. Thus, about 1 mg of liver-derived chromosome DNA was obtained. This DNA (10 µg) was partially cleaved with restriction enzyme Sau3AI, and the resulting product was subjected to equilibrium density gradient centrifugation using CsCl. Fractions containing DNA fragments having lengths of 10 to 20 kb were selected and introduced into fragments obtained by cleaving phage charon 28 DNA with BamHI and used as a vector. This reaction called "ligation" was conducted at 15° C. for 16 hours. The charon 28 vector into which the *Xenopus laevis* chromosome DNA was thus introduced was contained in a phage head (in vitro packaging). This procedure was carried out by using a commercial packaging kit (Gigapack Gold, Stratagene). This recombinant phage was amplified by infection with *E. coli* LE392. Specifically, the phage was mixed with excess LE392 to allow LE392 to adsorb the phage at 37° C. for 10 minutes. Then, the mixture was plated on NZYM medium (containing 13% agar), followed by incubation overnight.

(2) Screening

The total number of the phage clones was estimated to be about 1,000,000 from the number of the plaques produced in a dish. As a probe (DNA used for detection of a desired gene by hybridization), there was used rat activin βA cDNA [*Molecular Endocrinology* 1, 388–396 (1987)] labeled with $^{32}p$ by a random priming method. The plaques transcribed from the dish to a nitrocellulose membrane were returned to neutrality (0.2M Tris, 0.6M NaCl, pH 7.4) through alkali treatment (immersion in 0.1N NaOH, 0.6M NaCl for 30 seconds). After completion of the treatment described above, the membrane was heated in a vacuum thermostat at 80° C. for 1 hour. After heating, the membrane was immersed in a hybridization solution (50% formamide, 5× Denhardt's solution, 5× SSPE, 0.1% SDS, 100 µg/ml denatured salmon sperum DNA) to incubate it at 42° C. for 4 hours. Then, the membrane was allowed to stand in the mixture solution of the above hybridization solution and the DNA probe at 60° C. overnight. This procedure was carried out in a plastic bag. The next day, the nitrocellulose membrane was taken out of the bag, and washed with a solution of 2× SSC and 0.1% SDS for 15 minutes and with a solution of 0.1× SSC and 0.1% SDS for 15 minutes, increasing the temperature stepwise, until the cpm value of the membrane reached about 1,000 cpm. After washing, the washing solution was removed by filter paper, and then the membrane was subjected to autoradiography. The plaque containing the desired gene was identified by exposure of a Fuji X-ray film. The genes were cloned by repetition of the above plaque hybridization.

20× SSC contains 0.3M sodium citrate (pH 7.0) and 3M NaCl; 20× SSPE contains 0.2M sodium phosphate, 20 m EDTA and 3M NaCl (pH 7.4); and Denhardt's solution contains 1% Ficoll, 1% polyvinylpyrrolidone and 1% BSA (Pentex Fraction V).

(3) Determination of Nucleotide Sequence (Sequencing)

All of the five isolated clones A4, A5, B9, C4 and M3 were each subcloned into plasmid pUC19. In subcloning each clone into plasmid pUC19, subcloning was carried out utilizing a restriction enzyme recognition site which produced a fragment hybridized with the probe for each clone. However, for cloning clone A4, a commercial BglII linker was used to ligate a SmaI site.

The plasmids were each transformed into competent cell HB101 (*E. coli*) prepared by the rubidium chloride method to obtain five kinds of transformants *E. coli* HB101/pXar3 (coding for protein M3), *E. coli* HB101/pXar4 (coding for protein A4), *E. coli* HB10t/pXar9 (coding for protein A9), *E. coli* HB101/pXar9 (coding for protein B9) and *E. coli* HB101/pXar14 (coding for protein-C4), respectively.

For determination of the nucleotide sequence, a deletion mutant of each clone was prepared, and the shortest of fragment hybridized with the probe was selected. The nucleotide sequence was determined from pUC19 by the direct Sanger method (or the dideoxy method).

For translation of the nucleotide sequence to an amino acid sequence or for screening of homology, a software for genetic analysis (GENETYX Nippon SDC) was used.

| | Homology at Nucleic Acid Level | | | | | |
|---|---|---|---|---|---|---|
| TYX nucleo- tide | Rat Act βA, % | Rat Act βA, % | Human TGF β2, % | xVgl % | M3 % | A4 % |
| A5 | 70.3 (101) | 47.5 (314) | 43.8 (169) | 48.5 (171) | 54.7 (258) | 63.7 (328) |
| A4 | 69.5 (0.5) | — | — | — | 55.4 (251) | |
| M3 | 63.6 (332) | 53.9 (672) | 33.1 (689) | — | | |

In the above table, numerical values in parentheses indicate the length compared (bp).

| | Homology at Amino Acid Level | | | | | |
|---|---|---|---|---|---|---|
| TYX nucleo- tide | Rat Act βA, % | Rat Act βA, % | Human TGF β2, % | xVgl % | M3 % | A4 % |
| A5 | 58.8 (34) | 44.1 (34) | 37.2 (43) | 50.0 (38) | 26.0 (77) | 67.6 (68) |
| A4 | 41.3 (63) | 44.1 (34) | 39.5 (43) | 52.6 (38) | 30.3 (66) | |
| M3 | 50.3 (149) | 49.4 (162) | 32.8 (128) | 40.6 (106) | | |

In the above table, numerical values in parentheses indicate the length compared (bp).

EXAMPLE 2

Preparation of *Xenopus laevis* Unfertilized Egg-Derived DNA Library (1) Preparation of *Xenopus laevis* BMP-2A Probe A probe was prepared by fragmentation of chromosome DNA Xar14 coding for *Xenopus laevis* BMP-2A with restriction enzymes PstI and HindIII, and three kinds of cDNAs, Xbr22, Xbr23 and Xbr41 were isolated by screening of a *Xenopus laevis* unfertilized egg cDNA library by a hybridization method. The comparison with the structure of the *Xenopus laevis* BMP chromosome DNA already isolated revealed that Xbr22, Xbr23 and Xbr41 coded for proteins having homology with *Xenopus laevis* BMP-2A, *Xenopus laevis* BMP-2B and mouse Vgr-1 reported by Lyon et al. [*Proc. Natl. Acad. Sci. U.S.A.* 806, 4554–4558 (1989)], respectively.

The *Xenopus laevis* unfertilized egg cDNA library was provided by the Salk Institute (C. Kintner). This library was prepared based on λgt10. This recombinant phage was amplified by infection with *E. coli* NM514. Specifically, the phage was mixed with excess NM514 to allow NM514 to adsorb the phage at 37° C. for 10 minutes. Then, the mixture was plated on NZYM medium (containing 13% agar), followed by incubation overnight.

(2) Screening

The total number of the phage clones was estimated to be about 1,200,000 from the number of the plaques produced in a dish. As a probe (DNA used for detection of a desired gene by hybridization), there was used a DNA fragment (185 bp) obtained by cleaving Xar14 with restriction enzymes PstI and HindIII and labeled with $^{32}$p by a random priming method. The plaques transcribed from the dish to a nitrocellulose membrane were returned to neutrality (0.2M Tris, 0.6M NaCl, pH 7.4) through alkali treatment (immersion in 0.1N NaOH, 0.6M NaCl for 30 seconds). After completion of the treatment described above, the membrane was heated in a vacuum thermostat at 80° C. for 1 hour. After heating, the membrane was immersed in a hybridization solution (50% formamide, 5× Denhardt's solution, 5× SSPE, 0.1% SDS, 100 µg/ml denatured salmon sperm DNA) to incubate it at 42° C. for 4 hours. Then, the membrane was allowed to stand in the mixture solution of the above hybridization solution and the DNA probe at 60° C. overnight. This procedure was carried out in a plastic bag. The next day, the nitrocellulose membrane was taken out of the bag, and washed with a solution of 2× SSC and 0.1% SDS for 15 minutes, increasing the temperature stepwise, until the cpm value of the membrane reached about 1,000 cpm. After washing, the washing solution was removed by filter paper, and then the membrane was subjected to autoradiography. The plaque containing the desired gene was identified by exposure of a Fuji X-ray film. The genes were cloned by repetition of the above plaque hybridization.

20× SSC contains 0.3M sodium citrate (pH 7.0) and 3M NaCl; 20× SSPE contains 0.2M sodium phosphate, 20 m EDTA and 3M NaCl (pH 7.4); and Denhardt's solution contains 1% Ficoll, 1% polyvinylpyrrolidone and 1% BSA (Pentex Fraction V).

(3) Determination of Nucleotide Sequence (Sequencing)

All of the three isolated clones Xbr22, Xbr23 and Xbr41 were each subcloned into plasmid puc19. In subcloning each clone into plasmid pUC19, subcloning was carried out utilizing a restriction enzyme recognition site which produced a fragment hybridized with the probe for each clone.

The plasmids were each transformed into competent cell HB101 (*E. coli*) prepared by the rubidium chloride method to obtain three kinds of transformants *E. coli* HB101/pXbr22 (coding for *Xenopus laevis* BMP-2A), *E. coli* HB101/pXbr23 (coding for *Xenopus laevis* BMP-2B) and *E. coli* HB101/pXbr41 (coding for protein *Xenopus laevis* Vgr-1), respectively.

For determination of the nucleotide sequence, a deletion mutant of each clone was prepared, and the shortest fragment that hybridized with the probe was selected. The nucleotide sequence was determined from pUC19 by the direct Sanger method (or the dideoxy method.).

For translation of the nucleotide sequence to an amino acid sequence or for screening of homology, a software for genetic analysis (GENETYX, Nippon SDC) was used.

FIGS. 2(6) to 2(8) show the respective nucleotide sequences, and FIGS. 4 (VI) to 4 (VIII) show the respective amino acid sequences.

EXAMPLE 3

In order to examine the biological activity of the *Xenopus laevis* BMP-related gene products, each of Xbr22, Xbr23 and Xbr41 cDNAS was inserted into expression vector pCDM8 (Invitrogen, U.S.A.) for animal cells, and expressed in a COS cell(African green monkey kidney cell). The resulting culture supernatant was used for determination of the biological activity.

Each of the Xbr22, Xbr23 and Xbr41 cDNAs to which XhoI linkers were ligated at both ends thereof was inserted into the XhoI restriction enzyme-cleaving site of pCDM8 to use it for transfection (introduction of DNA). 3×10$^6$ cells were subcultured in a 100 mm diameter plastic dish, and the medium was removed after 24 hours, followed by washing once with 10 ml of TBS (Tris-buffered saline). 300 µl of a DNA solution (1.5 µg DNA) diluted with TBS was mixed with 300 µl of a 0.1% DEAE-dextran solution, and the combined solution was added dropwise to the cells. After standing at ordinary temperature for 15 minutes, the cells were washed once with 300 μl of TBS, and then incubated in Dulbecco's modified Eagle's medium (DMEM, containing 10% FBS, 100 U/ml penicillin, 100 mcg/ml streptomycin and 100 uM chloroquine). After 3 hours, the cells were washed twice with TBS and incubated in DMEM (containing 10% FBS, 100 U/ml penicillin and 100 mcg/ml streptomycin). After 24 hours, the cells were washed three times with TBS and incubated in DMEM (containing 100 U/ml penicillin and 100 mcg/ml streptomycin) for 4 days, followed by recovery of the medium. The recovered medium was centrifuged at 2,000 rpm for 5 minutes to obtain a culture supernatant.

The culture supernatant thus obtained was used for determination of the biological activity as a sample containing Xenopus laevis BMP2-A, BMP-2B or protein Vgr-1. Namely, each of the samples was added to the medium of rabbit chondrocytes in monolayer cultures [Y. Kato et al., Exp. Cell Res. 130, 73–81 (1980); Y. Kato et al., J. Biol. Chem. 265, 5903–5909 (1990)] to examine their effect on the synthesis of proteoglycan, the main component of a cartilage matrix. As a result, the control in which the COS cell was transfected with the expression vector alone and the medium conditioned by untreated COS cells did not affect the synthesis of proteoglycan, as shown in the following table. In contrast, the above three kinds of proteins obtained in the present invention strongly promoted the synthesis of proteoglycan by the cartilage cells. The maximum activity of Xenopus laevis BMP-2A, BMP- 2B and Vgr-1 was stronger than that of TGF-beta-1. The synthesis of proteoglycan was determined by measuring $^{35}$S-sulfate incorporation into glycosaminoglycans [Y. Kato et al., Exp. Cell Res. 130, 73–81 (1980); Y. Kato et al., J. Biol. Chem. 265, 5903–5909 (1990)]. These results show that the BMPs of Xenopus laevis promote the differentiation of cartilages, and suggest that the BMPs of other animals have similar effects. The BMPs are therefore expected to be applied to therapeutic agents for healing acceleration of fractures and for various diseases of cartilages and bones (such as arthritis and osteoporosis).

Kind of Cell

Rabbit costal chondrocytes maintained on 6-mm diameter plastic wells.

Kind of Marker $^{35}$S 1 μCi/ in 100 μl medium per well Kind of Medium

A 1:1 (V/V) mixture of DMEM and Ham's F-12 medium supplemented with 0.3% fetal bovine serum.

| No. | Additive | Count | | | Mean ± S.D. | % to Control |
|---|---|---|---|---|---|---|
| 1 | Control | 5193 | 4328 | 4269 | 4695 ± 351 | 100 |
|   |          | 4565 | 4727 | 5089 |            |     |
| 2 | xBMP2A 1 5 μl | 2362 | 2749 | 2758 | 2362 ± 185 | 56 |
| 3 | xBMP2A ⅓ 5 μl | 12198 | 15502 | 21891 | 16530 ± 4023 | 352 |
| 4 | xBMP2A 1/10 5 μl | 10004 | 9738 | 8848 | 9530 ± 494 | 203 |
| 5 | xBMP2B 1 5 μl | 3171 | 2906 | 3219 | 3099 ± 138 | 66 |
| 6 | xBMP2B ⅓ 5 μl | 11315 | 9750 | 13139 | 11401 ± 1385 | 243 |
| 7 | xBMP2B 1/10 5 μl | 12426 | 13457 | 13324 | 13069 ± 458 | 278 |
| 8 | xVgr-1 1 5 μl | 5188 | 2833 | 4416 | 4146 ± 980 | 88 |
| 9 | xVgr-1 ⅓ 5 μl | 7486 | 8834 | 7202 | 7841 ± 712 | 167 |
| 10 | xVgr-1 10 5 μl | 15286 | 15645 | 13032 | 14654 ± 1156 | 312 |
| 11 | pCDM8 5 μl | 3604 | 2694 | 2927 | 3075 ± 386 | 65 |
| 12 | pCMD8 1 μl | 2637 | 4219 | | 3428 ± 791 | 73 |
| 13 | DNA(-) 5 μl | 3625 | 4050 | 4714 | 4130 ± 448 | 88 |
| 14 | DNA(-) 1 μl | 5695 | 4657 | | 5176 ± 519 | 110 |
| 15 | DME 5 μl | 3614 | 8963 | 3850 | 5476 ± 2468 | 117 |
| 16 | DME 1 μl | 4384 | 3874 | 5760 | 4675 ± 799 | 100 |
| 17 | TGF-B1 3 ng/ml | 9381 | 12474 | 10922 | | |
|    |                | 10058 | 11546 | 11155 | 10923 ± 998 | 233 |
| 18 | Ins. 5 g/ml | 19431 | 20476 | 22746 | | |
|    |             | 25066 | 27835 | 24965 | 23420 ± 2876 | 499 |
| 19 | Ins. 3 g/ml | 13620 | 15379 | 11987 | | |
|    |             | 11240 | 12699 | 12666 | 12932 ± 1313 | 275 | pCDM8: A culture solution of the cells into which pCDM8 is introduced as a vector DNA(-): A culture solution which is in contact with the cells, which do not produce the BMPs DME: A solution which is not in contact with the cells Ins.: Insulin Experiments Procedure Rabbit chondrocytes were isolated from growth plates of ribs of 3- to 4- week old male New Zealand rabbits, as previously described (Y. Kato et al. Exp. Cell Res.). Cells were seeded at a density $10^4$ cells / 6-mm diameter plastic culture well in 0.1 ml of Eagle's minimum essential medium (MEM) supplemented with 10% fetal bovine serum and antibiotics. When cultures became confluent, the cells were preincubated for 24 hours in 0.1 ml of a 1:1 mixture of DMEM and Ham's F-12 medium supplemented with 0.3% fetal bovine serum (DF). The cells were then transferred to 0.1 ml of the same medium (DF) supplemented with 1 or 5 μl of the medium that was conditioned by various COS cells: [The conditioned medium was diluted or not diluted with DMEM (a final concentration of 10 or 30%)]. After 3 hours, 5 μl of DMEM supplemented with 1μCi of $^{35}SO_4^{2-}$ was also added, and incubation was continued for a further 17 hours (Y. Kato et al. Exp. Cell Res.).

The following references, which are referred to for their disclosures at various points in this application, are incorporated herein by reference.

J. Endocrinology 124, 2991–2994 (1989)

J. Bone Mineral Res. 4, S-259 (1989)

J. Biol. Chem. 281, 5693–5695 (1986)

Science 242, 1528–1534 (1989)

Bio-chemistry 18, 5294 (1979)

Molecular and Cellular Biology 2, 161 (1979)
Molecular and Cellular Biology 3, 280 (1983)
Gene 2, 95 (1977)
Gene 4, 121 (1978)
Gene 19, 259 (1982)
Biochemical and Biophysical Research Communication 112, 678 (1983)
Proc. Natl. Acad. Sci. U.S.A. 80, 1194 (1983)
Molecular Cloning, Cold Spring Harbor Laboratory, p.239 (1982)
DNA Cloning, A Practical Approach 1, 49 (1985)
Proc. Natl. Acad. Sci. U.S.A. 60, 160 (1968)
Nucleic Acids Research 9, 309 (1981)
Journal of Molecular Biology 120, 517 (1978)
Journal of Molecular Biology 41, 459 (1969)
Genetics 39, 440 (1954)
Gene 24, 255 (1983)
Journal of Biochemistry 95, 87 (1984)
Molecular Cloning, Cold Spring harbor Laboratory, p.249 (1982)
Proc. Natl. Acad. Sci. U.S.A. 74, 560 (1977)
Proc. Natl. Acad. Sci. U.S.A. 69, 2110 (1972)
Gene 17, 107 (1982)
Molecular & General Genetics 168, 111 (1979)
Proc. Natl. Acad. Sci. U.S.A. 75, 1929 (1978)
Virology 52, 456 (1973)
Journal of Experiments in Molecular Genetics 431–433, Cold Spring Harbor Laboratory, New York, 1972
Proc. Natl. Acad. Sci. U.S.A. 77, 4505 (1980)
Science 122, 501 (1952)
Virology 8, 396 (1959)
Journal of the American Medical Association 199, 519 (1967)
Proceeding of the Society for the Biological Medicine 73, 1 (1950)
Proc. Natl. Acad. Sci. U.S.A. 807, 2220–2224 (1990)
Molecular Endocrinology , 1388–396 (1987)
Proc. Natl. Acad. Sci. U.S.A. 806, 4554–4558 (1989)
Exp. Cell Res. 130, 73–81 (1980)
J. Biol. Chem. 265, 5903–5909 (1990)

What is claimed is:

1. An essentially purified and isolated *Xenopus laevis* bone morphogenetic protein (BMP) selected from the group of BMPs consisting of BMP-2A, BMP-2B, and Vgr-1, wherein BMP-2A corresponds to Gln Lys Arg Gln Ala Arg His Lys Gln Arg Lys Arg Leu Lys Ser Ser Cys Arg Arg His Pro Leu Tyr Val Asp Phe Ser Asp Val Gly Trp Asn Asp Trp Ile Val Ala Pro Pro Gly Tyr His Ala Phe Tyr Cys His Gly Glu Cys Pro Phe Pro Leu Ala Asp His Leu Asn Ser Thr Asn His Ala Ile Val Gln Thr Leu Val Asn Ser Val Asn Thr Asn Ile Pro Lys Ala Cys Cys Val Pro Thr Glu Leu Ser Ala Ile Ser Met Leu Tyr Leu Asp Glu Asn Glu Lys Val Val Leu Lys Asn Tyr Gln Asp Met Val Val Glu Gly Cys Gly Cys Arg, BMP-2B corresponds to Ser Pro Lys Gln Gln Arg Pro Arg Lys Lys Asn Lys His Cys Arg Arg His Ser Leu Tyr Val Asp Phe Ser Asp Val Gly Trp Asn Asp Trp Ile Val Ala Pro Pro Gly Tyr Gln Ala Phe Tyr Cys His Gly Asp Cys Pro Phe Pro Leu Ala Asp His Leu Asn Ser Thr Asn His Ala Ile Val Gln Thr Leu Val Asn Ser Val Asn Ser Ser Ile Pro Lys Ala Cys Cys Val Pro Thr Glu Leu Ser Ala Ile Ser Met Leu Tyr Leu Asp Glu Tyr Asp Lys Val Val Leu Lys Asn Tyr Gln Glu Met Val Val Glu Gly Cys Gly Cys Arg, and Vgr-1 corresponds to His Glu Leu Phe Val Ser Phe Arg Asp Leu Gly Trp Gln Asp Trp Ile Ile Ala Pro Glu Gly Tyr Ala Ala Tyr Tyr Cys Asp Gly Glu Cys Ala Phe Pro Leu Asn Ser Phe Met Asn Ala Thr Asn His Ala Ile Val Gln Thr Leu Val His Phe Ile Asn Pro Glu Thr Val Pro Lys Pro Cys Cys Ala Pro Thr Gln Leu Asn Gly Ile Ser Val Leu Tyr Phe Asp Asp Ser Ala Asn Val Ile Leu Lys Lys Tyr Lys Asn Met Val Val Gln Ala Cys Gly Cys His.

2. A composition for therapy of fracture or osteoporosis which contains an effective amount of the protein according to claim 1 and pharmaceutically acceptable additional components.

3. A method for promoting the synthesis of proteoglycan in cartilage cells by administering an effective amount of the protein according to claim 1 to a mammal in need thereof.

4. A protein according to claim 1, wherein the protein is purified and isolated by utilizing differences in solubility, differences in molecular weight, differences in electric charge, difference in specific affinity, differences in hydrophobicity or differences in isoelectric point.

5. The protein according to claim 4, wherein the difference in solubility is determined by salt precipitation or solvent precipitation.

6. The protein according to claim 4, wherein the difference in molecular weight is determined by dialysis, ultra filtration, gel electrophoresis or SDS-polyacrylamide gel electrophoresis.

7. The protein according to claim 4, wherein the difference in electric charge is determined by ion-exchange column chromatography.

8. The protein according to claim 4, wherein the difference in specific affinity is determined by affinity chromatography.

9. The protein according to claim 4, wherein the difference in hydrophobicity is determined by reverse phase high performance liquid chromatography.

10. The protein according to claim 4, wherein the difference in isoelectric point is determined by isoelectro-focusing electrophoresis.

11. A protein according to claim 1, wherein the protein is purified and isolated by using an antibody.

12. The protein according to claim 11, wherein the antibody is to a fused protein.

13. An essentially purified and isolated *Xenopus Laevis* Vgr-1 bone morphogenic protein which corresponds to the sequence His Glu Leu Phe Val Ser Phe Arg Asp Leu Gly Trp Gln Asp Trp Ile Ile Ala Pro Glu Gly Tyr Ala Ala Tyr Tyr Cys Asp Gly Glu Cys Ala Phe Pro Leu Asn Ser Phe Met Asn Ala Thr Asn His Ala Ile Val Gln Thr Leu Val His Phe Ile Asn Pro Glu Thr Val Pro Lys Pro Cys Cys Ala Pro Thr Gln Leu Asn Gly Ile Ser Val Leu Tyr Phe Asp Asp Ser Ala Asn Val Ile Leu Lys Lys Tyr Lys Asn Met Val Val Gln Ala Cys Gly Cys His.

14. A composition for therapy of fracture or osteoporosis which contains an effective amount of the protein of claim 13 and pharmaceutically acceptable additional components.

15. A method for promoting the synthesis of proteoglycan in cartilage cells by administering an effective amount of the protein of claim 13 to a mammal in need thereof.

16. The protein of claim 13, wherein the protein is purified and isolated by using a purification method comprising utilizing differences in solubility, differences in molecular weight, differences in electric charge, differences in specific affinity, differences in hydrobicity, and differences in isoelectric point.

17. The protein of claim 13, wherein the protein is purified and isolated by using an antibody.

18. The protein of claim 17, wherein the antibody is to a fused protein.

* * * * *

UNITED STATES PATENT AND TRADEMARK OFFICE
CERTIFICATE OF CORRECTION

PATENT NO. : 5,453,419
DATED : September 26, 1995
INVENTOR(S) : Kazuo MURAKAMI, et al.

It is certified that error appears in the above-identified patent and that said Letters Patent is hereby corrected as shown below:

On the title page, item [73] Assignee: should read --Taiheiyo Cement Corporation Tokyo, Japan; and Takeda Chemical Industries, Ltd., Osaka, Japan--.

Signed and Sealed this

Twenty-seventh Day of April, 1999

*Attest:*

Q. TODD DICKINSON

*Attesting Officer*     *Acting Commissioner of Patents and Trademarks*